(12) United States Patent
Muse et al.

(10) Patent No.: US 12,046,372 B2
(45) Date of Patent: Jul. 23, 2024

(54) MACHINE-LEARNING-BASED PREDICTIVE BEHAVIORAL MONITORING

(71) Applicant: Optum, Inc., Minnetonka, MN (US)

(72) Inventors: Jon Kevin Muse, Thompson Station, TN (US); Gregory J. Boss, Saginaw, MI (US); Paul J. Godden, London (GB); Mark Gregory Megerian, Rochester, MN (US)

(73) Assignee: Optum, Inc., Minnetonka, MN (US)

( * ) Notice: Subject to any disclaimer, the term of this patent is extended or adjusted under 35 U.S.C. 154(b) by 412 days.

(21) Appl. No.: 16/999,133

(22) Filed: Aug. 21, 2020

(65) Prior Publication Data

US 2022/0059230 A1 Feb. 24, 2022

(51) Int. Cl.
*G16H 50/20* (2018.01)
*G16H 50/30* (2018.01)

(52) U.S. Cl.
CPC ............. *G16H 50/30* (2018.01); *G16H 50/20* (2018.01)

(58) Field of Classification Search
CPC ........ G16H 10/40; G16H 10/60; G16H 50/20; G16H 50/30; G16H 50/70; G16H 70/20; G16B 5/20; G16B 40/00; G06N 3/08; G06N 20/00; G06Q 10/10; G06Q 40/00; G06Q 40/08; G06Q 50/16; G06F 15/18
USPC .......................................................... 705/2, 3
See application file for complete search history.

(56) References Cited

U.S. PATENT DOCUMENTS

| | | |
|---|---|---|
| 7,987,122 B2 | 7/2011 | Bevente et al. |
| 8,204,768 B1 | 6/2012 | Grinberg |
| 8,504,461 B1 | 8/2013 | Schulz et al. |
| 8,930,205 B1 | 1/2015 | Klieman |
| 10,572,947 B1 * | 2/2020 | Berends ............... G06Q 50/163 |
| 2006/0026036 A1 | 2/2006 | Mahmood |

(Continued)

FOREIGN PATENT DOCUMENTS

| | | |
|---|---|---|
| CN | 110390425 A * | 10/2019 |
| EP | 3019970 B1 | 7/2018 |

OTHER PUBLICATIONS

Alqahtani, Fayez Hussain. "The Application Of The Internet Of Things In Healthcare," International Journal Of Computer Applications (0975-8887), vol. 180, No. 18, Feb. 2018, pp. 19-23.

(Continued)

*Primary Examiner* — Alaaeldin M Elshaer
(74) *Attorney, Agent, or Firm* — ALSTON & BIRD LLP

(57) ABSTRACT

Systems and methods are configured to perform machine-learning-based predictive behavioral response. In various embodiments, one or more behavioral monitoring data objects are identified and processed using a behavioral pattern prediction machine learning model to generate a behavioral pattern prediction model. The behavioral pattern prediction model is processed using a risk generation machine learning model to generate a risk model, wherein: (i) the risk generation machine learning model is generated based at least in part by one or more risk factors, and (ii) the risk model comprises a per-risk factor score for each risk factor of the one or more risk factors. The risk model is processed using an adjustment generation machine learning model to generate an adjustment model and one or more prediction-based actions are performed based on the adjustment model.

20 Claims, 16 Drawing Sheets

(56) References Cited

U.S. PATENT DOCUMENTS

| | | | |
|---|---|---|---|
| 2006/0064332 | A1 | 3/2006 | Schoenbaum et al. |
| 2007/0072156 | A1* | 3/2007 | Kaufman ............... G16H 20/60 434/236 |
| 2008/0027753 | A1 | 1/2008 | Dean |
| 2010/0042438 | A1 | 2/2010 | Moore et al. |
| 2011/0161095 | A1 | 6/2011 | Line et al. |
| 2012/0012648 | A1 | 1/2012 | Collins et al. |
| 2012/0130198 | A1 | 5/2012 | Beaulé |
| 2013/0304618 | A1* | 11/2013 | Mastrogiovanni ...... G06T 11/60 705/35 |
| 2014/0006050 | A1 | 1/2014 | Feinschreiber et al. |
| 2014/0372133 | A1* | 12/2014 | Austrum ............... G16H 50/30 705/2 |
| 2016/0148317 | A1 | 5/2016 | Benway et al. |
| 2016/0269491 | A1 | 9/2016 | Eom et al. |
| 2016/0378942 | A1 | 12/2016 | Srinivas et al. |
| 2017/0004279 | A1 | 1/2017 | Pingali et al. |
| 2017/0140114 | A1* | 5/2017 | Are ......................... G16H 50/20 |
| 2017/0147777 | A1* | 5/2017 | Kim ......................... G16H 50/30 |
| 2017/0177808 | A1 | 6/2017 | Irwin et al. |
| 2017/0186120 | A1* | 6/2017 | Reid ...................... G16H 10/60 |
| 2017/0262609 | A1 | 9/2017 | Perlroth et al. |
| 2017/0286608 | A1 | 10/2017 | Srinivas et al. |
| 2018/0033087 | A1 | 2/2018 | Delinselle et al. |
| 2019/0180852 | A1 | 6/2019 | Jiao et al. |
| 2019/0333614 | A1 | 10/2019 | Burger et al. |
| 2019/0340684 | A1* | 11/2019 | Belanger .............. G06N 3/0445 |
| 2020/0027181 | A1 | 1/2020 | Ohnemus et al. |
| 2020/0074573 | A1 | 3/2020 | Op Den Buijs et al. |
| 2020/0104935 | A1 | 4/2020 | Schmitt et al. |
| 2020/0168335 | A1* | 5/2020 | Lassoued ............... G16H 40/67 |
| 2021/0256615 | A1* | 8/2021 | Hayward ............... G08B 19/00 |

OTHER PUBLICATIONS

Chen, James. Autoregressive Integrated Moving Average (ARIMA), Investopedia, Apr. 13, 2019, (6 pages), [article, online]. [Retrieved from the Internet Sep. 6, 2020] <URL: https://www.investopedia.com/terms/a/autoregressive-integrated-moving-average-arima.asp>.

Dimitrov, Dimiter V. "Medical Internet Of Things and Big Data In Healthcare," Healthcare Informatics Research, vol. 22, No. 3, (2016), pp. 156-163. DOI: 10.4258/hir.2016.22.3.156.

Glied, Sherry A. et al. "The Effect Of Health Savings Accounts On Health Insurance Coverage," The Commonwealth Fund, Apr. 2005, vol. 811, pp. 1-8. [Retrieved from the Internet Sep. 6, 2020] <https://www.commonwealthfund.org/sites/default/files/documents/_media_files_publications_issue_brief_2005_apr_the_effect_of_health_savings_accounts_on_health_insurance_coverage_811_glied_effect_hlt_savings_accounts_coverage_pdf.pdf>.

Leive, Adam. "Essay In The Economics Of Health, Risk, and Behavior," Publicly Accessible Penn Dissertations, (2016), (153 pages). [Retrieved from the Internet Sep. 6, 2020] <URL: https://repository.upenn.edu/cgi/viewcontent.cgi?article=3627&context=edissertations>.

Lowsky, David J. et al. "Health Savings Accounts: Consumer Contribution Strategies and Policy Implications," MDM Policy & Practice, vol. 3, Issue 2, Jul.-Dec. 2018, pp. 1-14. DOI: 10.1177/2381468318809373.

McDonald, Carol. "Applying Machine Learning To Streaming IoT For Connected Medical Devices," MapR Technologies, Inc., Jul. 25, 2017, (16 pages). [Retrieved from the Internet Sep. 6, 2020] <URL: https://web.archive.org/web/20190805190413/https://mapr.com/blog/ml-iot-connected-medical-devices/>.

Rosebrock, Adrian. "Keras: Multiple Inputs and Mixed Data," pyimagesearch, Feb. 4, 2019, (66 pages), [article, online]. [Retrieved from the Internet Sep. 6, 2020] <URL: https://www.pyimagesearch.com/2019/02/04/keras-multiple-inputs-and-mixed-data/>.

Vitabile, Salavatore et al. "Medical Data Processing and Analysis For Remote Health and Activities Monitoring," In High-Performance Modelling and Simulation for Big Data Applications, (2019), pp. 186-220. Springer, Cham.

Yochze. "How To Apply Continual Learning To Your Machine Learning Models," Towards Data Science, Jul. 11, 2019, (8 pages), [article, online]. [Retrieved from the Internet Sep. 6, 2020] <URL: https://towardsdatascience.com/how-to-apply-continual-learning-to-your-machine-learning-models-4754adcd7f7f>.

* cited by examiner

MACHINE-LEARNING-BASED PREDICTIVE BEHAVIORAL MONITORING

TECHNOLOGICAL FIELD

Embodiments of the present disclosure generally relate to machine-learning-based user behavioral monitoring systems. The inventors have developed solutions that increase the efficiency and reliability of existing user behavioral monitoring systems.

BACKGROUND

A need exists in the industry to address technical problems related to performing predictive behavioral response in an efficient and reliable manner. It is with respect to these considerations and others that the disclosure herein is presented.

BRIEF SUMMARY

In general, embodiments of the present disclosure provide methods, apparatus, systems, computing devices, computing entities, and/or the like for performing predictive behavioral monitoring. Certain embodiments of the present disclosure utilize systems, methods, and computer program products that perform predictive behavioral monitoring using at least one of a medical conditions prediction machine learning model, a behavioral pattern prediction machine learning model, a risk generation machine learning model, and an adjustment generation machine learning model.

In accordance with one aspect of the disclosure, a computer-implemented method for predictive behavioral response is provided. In various embodiments, the method includes: receiving one or more behavioral monitoring data objects generated by one or more distributed behavioral monitoring devices; processing the one or more behavioral monitoring data objects using a behavioral pattern prediction machine learning model to generate a behavioral pattern prediction model, wherein the behavioral pattern prediction model identifies occurrences of an end user participating in one or more behaviors; and in response to generating the behavioral pattern prediction model: processing the one or more patterns of behavior for the one or more behaviors using a risk generation machine learning model to generate a risk model, wherein: (i) the risk generation machine learning model is generated based at least in part on one or more risk factors contributed to by the one or more behaviors, (ii) the risk model comprises a per-risk factor score for each risk factor of the one or more risk factors that identifies an effect of the one or more patterns of behavior, and (iii) each of the patterns of behavior identifies instances of the end user participating in a corresponding behavior of the one or more behaviors over a period of time; processing the risk model using an adjustment generation machine learning model to generate an adjustment model based on the risk model; and performing one or more prediction-based actions based on the adjustment model.

In accordance with another aspect of the present disclosure, an apparatus is provided. In various embodiments, the apparatus includes at least one processor and at least one memory including program code. The at least one memory and the program code are configured to, with the processor, cause the apparatus to at least: receive one or more behavioral monitoring data objects generated by one or more distributed behavioral monitoring devices; process the one or more behavioral monitoring data objects using a behavioral pattern prediction machine learning model to generate a behavioral pattern prediction model, wherein the behavioral pattern prediction model identifies occurrences of an end user participating in one or more behaviors; and in response to generating the behavioral pattern prediction model: process the one or more patterns of behavior for the one or more behaviors using a risk generation machine learning model to generate a risk model, wherein: (i) the risk generation machine learning model is generated based at least in part on one or more risk factors contributed to by the one or more behaviors, (ii) the risk model comprises a per-risk factor score for each risk factor of the one or more risk factors that identifies an effect of the one or more patterns of behavior, and (iii) each of the patterns of behavior identifies instances of the end user participating in a corresponding behavior of the one or more behaviors over a period of time; process the risk model using an adjustment generation machine learning model to generate an adjustment model based on the risk model; and have one or more prediction-based actions performed based on the adjustment model.

In accordance with yet another aspect of the present disclosure, a computer program product is provided. In particular embodiments, the computer program product includes at least one non-transitory computer-readable storage medium having computer-readable program code portions stored therein. The computer-readable program code portions configured to: receive one or more behavioral monitoring data objects generated by one or more distributed behavioral monitoring devices; process the one or more behavioral monitoring data objects using a behavioral pattern prediction machine learning model to generate a behavioral pattern prediction model, wherein the behavioral pattern prediction model identifies occurrences of an end user participating in one or more behaviors; and in response to generating the behavioral pattern prediction model: process the one or more patterns of behavior for the one or more behaviors using a risk generation machine learning model to generate a risk model, wherein: (i) the risk generation machine learning model is generated based at least in part on one or more risk factors contributed to by the one or more behaviors, (ii) the risk model comprises a per-risk factor score for each risk factor of the one or more risk factors that identifies an effect of the one or more patterns of behavior, and (iii) each of the patterns of behavior identifies instances of the end user participating in a corresponding behavior of the one or more behaviors over a period of time; process the risk model using an adjustment generation machine learning model to generate an adjustment model based on the risk model; and have one or more prediction-based actions performed based on the adjustment model.

In particular embodiments, the risk generation machine learning model is configured to generate the risk model by: generating a general risk model based on the one or more patterns of behavior; generating an individual risk model based on the one or more patterns of behavior in relation to the end user; and combining the general risk model and the individual risk model to generate the risk model. In addition, in particular embodiments, the adjustment generation machine learning model includes a time series prediction model and an adjustment application model. For instance, in some embodiments, the time series prediction model may be an autoregressive integrated moving average model. Accordingly, in particular embodiments, the adjustment generation machine learning model may generate the adjustment model by determining a projected contribution for a prospective period of time by using the time series prediction model and processing the projected contribution and the risk model using the adjustment application model to generate the adjustment model.

In some embodiments, the one or more risk factors are determined based on one or more medical conditions applicable to the end user and a health profile data object for the end user is processed using a medical conditions prediction machine learning model to identify the one or more medical conditions, wherein the medical conditions prediction machine learning model is configured to identify a probability for each of a plurality of medical conditions identifying a likelihood of the end user developing the medical condition. In some embodiments, the one or more prediction-based actions include automatically adjusting a current contribution rate to a financial instrument based on the adjustment model.

BRIEF DESCRIPTION OF THE SEVERAL VIEWS OF THE DRAWING(S)

Having thus described the disclosure in general terms, reference will now be made to the accompanying drawings, which are not necessarily drawn to scale, and wherein:

DETAILED DESCRIPTION OF SOME EXAMPLE EMBODIMENTS

Figure 1:
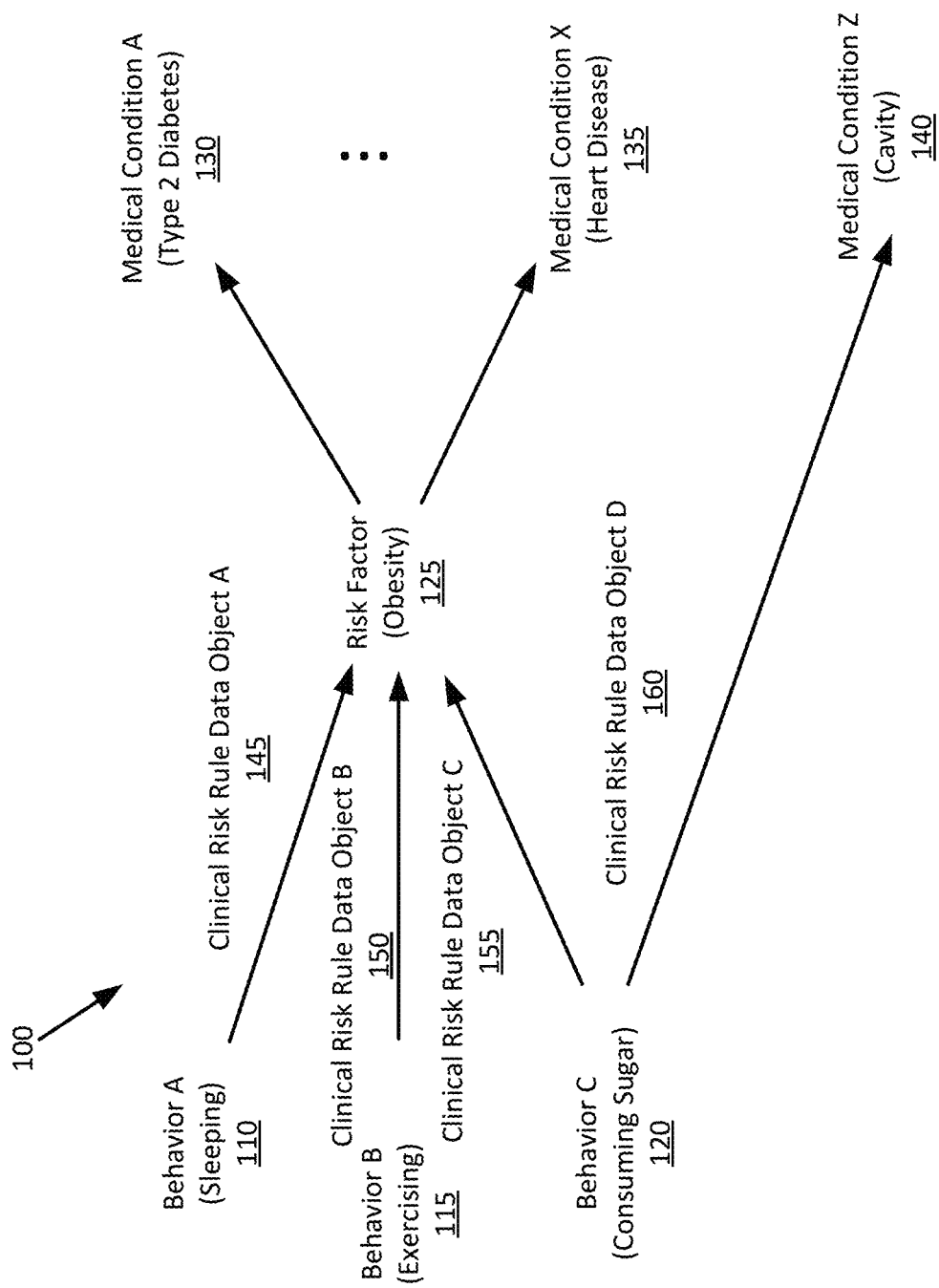
FIG. 1 is a diagram demonstrating relationships between behaviors, risk factors, and medical conditions.

Various embodiments of the present disclosure now will be described more fully hereinafter with reference to the accompanying drawings, in which some, but not all embodiments of the disclosure are shown. Indeed, the disclosure may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

Definitions of Certain Terms

The term "distributed behavioral monitoring device" may refer to a computing entity that is configured to capture one or more sensory information describing end user behavior and transmit the sensory information to a remote monitoring system, such as a predictive data analysis system. Examples of distributed behavioral monitoring devices include various Internet of Things (IoT) devices such as smartwatches or other wearable devices, smartphone devices, and the like.

The term "behavior" may refer to an action, conduct, or condition exhibited by an end user. In various embodiments, an end user's performance of behaviors is monitored to identify actions, conduct, or conditions exhibited by the end user that may contribute to a known risk. For example, an end user's consumption of sugary food items may be monitored to assess the end user's consumption of such items contributing to becoming obese. With that said, behaviors may be considered in combination with other behaviors in various embodiments in evaluating one or more risks. For example, an end user may go to the gym for an intensive weight training session and then drink a high-sugar "post-workout" energy drink. The gym session is beneficial with respect to the risk of obesity but regular consumption of such drinks may lead to a risk of tooth decay. Accordingly, behaviors may be characterized as either negative or positive with respect to their contribution to a risk. For example, a behavior that may be monitored is the level of activity (e.g., exercise) engaged in by an end user. Such behavior may be viewed as a positive contributor with respect to the end user developing obesity. That is to say, such behavior may be viewed as reducing the end user's likelihood of developing obesity. The term "instance" may refer to an occurrence of an end user performing a behavior.

The term "behavioral monitoring data object" may refer to a data object that describes end user behaviors captured by sensory components of a distributed behavioral monitoring device. For example, a particular behavioral monitoring data object may describe that an end user was present at a particular location during a particular period of time. Another example of a particular behavioral monitoring data object may describe an end user's performance in a particular physical activity (e.g., exercising) during a particular period of time. Yet another example of a particular behavioral monitoring data object may describe an end user purchasing and/or consuming a particular food item during a particular period of time. Such behavioral monitoring data objects may be captured in real time as the corresponding behaviors are being performed by the user end or after the fact, once the end user has performed the corresponding behaviors. Accordingly, behavioral monitoring data objects may represent mixed data types having different data formats such as, for example, categorical, textual, numerical, image, continuous, and the like. Furthermore, clinical evidence has shown that many devices used in collecting behavioral monitoring data objects, such as a device used in continuously monitoring blood glucose for example, can provide "high-grade" risk and/or benefit data.

The term "collection of behavior data object" may refer to a data object that represents previous instances of an end user performing a particular behavior. For example, a collection of behavior data object may describe occurrences of an end user purchasing/consuming sugary food items, participating in physical activity, or sleeping. Accordingly, a collection of behavior data object may represent the occurrences using some type of measurement such as, for example, the number of grams of sugar consumed by an end user, the number of minutes of physical activity the end user participated in over a defined time period, and the like.

The term "medical condition" may refer to a physiologic, mental, psychological state of an end user with respect to health. Thus, a medical condition may oftentimes entail a disease, disorder, illness or injury experienced by the end user. Manifestations of many medical conditions may be associated with specific symptoms and signs. Further, an end user's genetic profile may indicate the end user is predisposed with respect to various medical conditions, as well as provide a baseline risk profile for some well-established conditions in that the end user's genetic profile is generally fixed across a person's life.

The term "health profile data object" may refer to a data object that represents the current health state of an end user. The term "current health state" may refer to an overall picture of the end user's current health. For example, an end user's health profile data object may identify medical conditions currently being experienced by the end user, as well as history of medical conditions experienced in the past. In addition, the end user's health profile data object may provide physiological data collected on the end user such as height, weight, blood type, heart rate, blood pressure, and the like. Further, the end user's health profile data object may provide a genetic profile for the end user and/or medical conditions the end user may be predisposed to develop, as well as family medical history. Furthermore, the end user's health profile data object may provide behavioral habits of the end user. Accordingly, in particular embodiments, the end user's health profile data object may be periodically updated with recent health information gathered on the end user so that the data object better reflects the end user's current health state.

The term "medical conditions prediction machine learning model" may refer to a data object that describes parameters and/or hyper-parameters (e.g., defined operations) of a machine learning model that is configured to process a health profile data object for a particular end user to generate a medical conditions model for the end user. In some embodiments, the medical conditions prediction machine learning model may include a rule-based machine learning model that is configured to infer medical conditions the end user may be likely to develop based on identified risks factors associated with the medical conditions. Accordingly, in particular embodiments, the medical conditions prediction machine learning model may include a trained machine learning model (e.g., trained using past historical end user data across one or many end users) that is configured to process the health profile data object associated with the particular end user to generate the medical conditions model for the end user. For instance, pooling of de-identified data in a central repository may be used to enhance the model's prediction.

The term "medical conditions model" may refer to a data object that describes the medical condition scores for a group of defined medical conditions. Accordingly, a medical condition score describes a likelihood of an end user developing a corresponding medical condition. In some embodiments, a predictive data analysis system may define a group of medical conditions of interest. In some of the noted embodiments, the medical conditions model may be a data structure such as a vector or a tensor including a group of values, where each value in the group may represent a medical condition score for a corresponding medical condition. As described in greater detail herein, the medical conditions model may be used in particular embodiments in identifying risk factors for an end user that contribute to the medical conditions the end user may be susceptible in developing.

The term "behavioral pattern prediction machine learning model" may refer to a data object that describes parameters and/or hyper-parameters (e.g., defined operations) of a machine learning model that is configured to process one or more behavioral monitoring data objects associated with a particular end user collected during a particular time interval to generate a behavioral pattern prediction model for the particular end user and particular time interval. In some embodiments, the behavioral pattern prediction machine learning model may include a rule-based machine learning model that is configured to infer performance of particular behaviors by the end user based on defined patterns of behavioral monitoring data objects. For example, a particular behavioral pattern prediction machine learning model may be configured to infer that an end user has consumed ice cream when he or she is detected via particular behavioral monitoring data objects to be in a predefined vicinity of an ice cream store. As another example, a particular behavioral pattern prediction machine learning model may be configured to determine that an end user is running when a particular pattern of behavioral monitoring data objects indicates an above-threshold velocity of end user movement patterns. In some embodiments, the behavioral pattern prediction machine learning model may include a trained machine learning model (e.g., trained using past historical end user data across one or many end users) that is configured to process one or more behavioral monitoring data objects associated with a particular end user collected during a particular time interval to detect one or more behavioral patterns of the particular end user during the particular time interval. For example, a particular trained machine learning model may be configured to, in part, process one or more behavioral monitoring data objects associated with a particular end user collected during a particular time interval to generate a prediction about whether the particular end user is/was running during the particular time interval. In some embodiments, the behavioral pattern prediction machine learning model may be configured to process, in addition to behavioral monitoring data objects associated a particular end user and a particular time interval, data describing defined/detected habits of the particular end user in order to generate a behavioral pattern prediction model for the particular end user and particular time interval.

The term "behavioral pattern prediction model" may refer to a data object that describes an estimated/predicted pattern of end user behavior during a particular time interval. The data object may be determined using a behavioral pattern prediction machine learning model in accordance with at least one of one or more behavioral monitoring data objects associated with a particular end user and particular time interval and defined/detected habits of the particular end user. In some embodiments, a predictive data analysis system defines a set of candidate behaviors (i.e., a set of behaviors whose performance by an end user is of interest), and the behavioral pattern prediction model is a data structure such as a vector or a tensor that defines properties associated with occurrence or non-occurrence of the set of candidate behaviors. For example, in a particular predictive data analysis system, the set of candidate behaviors may include a calorie intake event, a running event, a prescription intake event, a water intake event, and a sleep event. In the noted example, the behavioral pattern prediction model may be a data structure such as a vector or tensor that includes the following values: (i) a first value that describes occurrence/non-occurrence of the calorie intake event with respect to a corresponding end user during the particular time interval, (ii) a second value that describes occurrence/non-occurrence of the running event with respect to the corresponding end user during the particular time interval, (iii) a third value that describes occurrence/non-occurrence of the prescription intake event with respect to the corresponding end user during the particular time interval, (iv) a fourth value that describes occurrence/non-occurrence of the water intake event with respect to the corresponding end user during the particular time interval, and (v) a fifth value that describes occurrence/non-occurrence of the sleep event with respect to the corresponding end user during the particular time interval.

The term "risk factor" may refer to a data object that describes a risk that is deemed to contribute to a medical condition of interest for an end user. For example, obesity is known to contribute to several medical conditions such as type 2 diabetes, heart disease, and liver disease. Various embodiments on the disclosure involve monitoring end users to determine whether they are trending towards one or more risk factors. The term "trending" may refer to an end user who is progressing towards a risk factor. For example, an end user may be progressing towards becoming obese.

The term "clinical risk rule data object" may refer to a data object representing a rule used in identifying when an end user is trending towards a risk factor. In various embodiments, a clinical risk rule data object may be associated with a particular behavior that is known to contribute to the risk factor. For example, a clinical risk rule data object may be defined with respect to consuming sugary food items leading to obesity. Further, a clinical risk rule data object may identify a threshold for the behavior that when exceeded by an end user conducting the behavior indicates the end user is trending towards the associated risk factor. The term "compound risk rule data object" may refer to a data object representing a combination of two or more clinical risk rule data objects.

The term "per-risk factor score" may refer to a data object that describes an estimated magnitude of the effect of a pattern of one or more behaviors on a corresponding risk factor. For example, a particular per-risk factor score may describe an estimated magnitude of the effect of a pattern of consuming sugary food items and lack of exercise for an end user has on the end user developing obesity.

The term "risk generation machine learning model" may refer to a data object that describes parameters and/or hyper-parameters (e.g., defined operations) of a machine learning model that is configured to process one or more collection of behavior data objects for a particular end user to generate a risk model for the particular end user. For instance, in some embodiments, the risk generation machine learning model includes a trained machine learning model that is configured to process one or more collection of behavior data objects and health profile data object for a particular end user to generate a risk model for the particular end user. In some embodiments, the risk generation machine learning model may include a rule-based machine learning model that is configured to infer risk of particular behaviors performed by the end user based on clinical risk rule data objects. Such inference may be developed based on input from clinical experts, research publications, etc. In particular embodiments, the risk generation machine learning model may generate a general risk model for the collection of behavior data objects, generate an individual risk model for the collection of behavior data objects in relation to the end user, and combine the general risk model and the individual risk model to generate the risk model. In some embodiments, the risk generation machine learning module generates the general risk model based on phenotype risk data and genetic risk data (e.g., risk data describing established risk alleles for a particular condition).

The term "risk model" may refer to a data object that describes the per-risk factor scores for a group of defined risk factors. In some embodiments, a predictive data analysis system may define a group of risk factors that are related to a group of medical conditions of interest for an end user. In some of the noted embodiments, the risk model may be a data structure such as a vector or a tensor including a group of values, where each value in the group describes a per-risk factor score for a corresponding risk factor. As described in greater detail herein, the risk model may be processed by an adjustment generation machine learning model to generate an adjustment model for a corresponding end user.

The term "opportunity cost" may refer to a cost of an end user performing a particular instance of a behavior that contributes to one or more risk factors and/or medical conditions.

The term "financial instrument" may refer to a valuative account used to hold monetary funds. For example, a financial instrument may be an HSA or FSA used as a savings vehicle for an end user who places pre-tax contributions into the account that can then be used to cover OPP medical expenses. In other instances, a financial instrument may simply be some type of banking account such as a savings account or checking account. Oftentimes such instruments allow for the monetary funds placed in them to accrue interest.

The term "adjustment generation machine learning model" may refer to a data object that describes parameters and/or hyper-parameters (e.g., defined operations) of a machine learning model that is configured to process a risk model for a particular end user to generate an adjustment model for the particular end user. In some embodiments, the adjustment generation machine learning model includes a rule-based machine learning model that includes, for each per-risk factor score defined by a risk model, a per-risk-score adjustment value. In some embodiments, the adjustment generation machine learning model is a trained machine learning model that is configured to process the risk model for the particular end user to generate the adjustment model for the end user.

The term "adjustment model" may refer to a data object that describes a desired effect of a particular risk model on a financial instrument of a corresponding end user. For example, a particular adjustment model may require the contributions to an HSA of a particular end user be increased based on the per-risk factor scores described by a corresponding risk model. As another example, a particular adjustment model may require the contributions to an FSA of a particular end user be increased based on the per-risk factor scored described in a corresponding risk model.

The term "current contribution rate" may refer to the rate at which an end user is currently making monetary contributions to a financial instrument. For example, the current contribution rate may refer to the rate at which an end user is currently making pre-taxed monetary contributions to an HSA. These contributions to the HSA are often used in covering OOP medical expenses incurred by the end user that are not covered by the end user's health insurance plan.

The term "required contribution amount" may refer to an amount that an end user must contribute to a financial instrument to cover OOP medical expenses expected to be incurred by developing one or more medical conditions.

The term "current medical plan data object" may refer to a data object that represents information on an end user's current medical insurance plan. For example, the current medical plan data object for an end user may indicate the end user is currently enrolled in a high or low deductible plan, a preferred providers organization (PPO) plan, or health maintenance organization (HMO) plan. In addition, the current medical plan data object may indicate conditions placed on the plan such as maximum OOP expenses that may be incurred by the end user in a year. Further, the current medical plan data object may indicate legal and/or policy restrictions placed on the end user's current medical insurance plan such as, for example, restrictions on changing the contribution rate to an HSA.

The term "contribution model" may refer to a data object that describes parameters and/or hyper-parameters of a model that enables determining a required contribution amount for one or more potential medical conditions that an individual may develop.

Exemplary Technical Contributions

Various embodiments of the present disclosure address technical problems related to performing predictive behavioral response in an efficient and reliable manner by utilizing disjoint machine learning models configured to perform condition identification, behavioral detection, risk generation, and adjustment generation. Performing all four of the noted tasks using the same machine learning model is likely to lead to a model that is both highly inefficient to train (i.e., requires a high amount of training data as well as a large number of training iterations) and subject to overfitting concerns.

Accordingly, various embodiments of the present disclosure overcome the noted challenges of utilizing a unitary machine learning model to perform condition identification, behavioral detection, risk generation, and adjustment generation by utilizing four machine learning models: one configured to perform condition identification; one configured to perform behavioral detection; one configured to perform risk generation; and one configured to perform adjustment generation. By utilizing the noted approach, embodiments of the present disclosure improve the efficiency and reliability of performing predictive behavioral response and make important contributions to the field of predictive behavioral response generally.

For example, in the Keras deep learning framework, a "multi-input model" is a deep learning implementation that features distinct models for different data items. For example, the multi-input model may include a convolutional neural network for image data and a recurrent network for text data. However, the output is a single classification. With this in mind, various embodiments as described herein implement multiple models to lead to multiple predictive elements within a risk prediction framework.

Moreover, deposits made to an HSA or FSA are important contributions for taxpayers, especially for those enrolled in high-deductible health plans (HDHP), but are often under-utilized. The term "financial instrument" is used throughout the remainder of the disclosure to represent such accounts. Although those of ordinary skill in the art will recognize this term is applicable to a number of different types of accounts. For example, various embodiments of the disclosure can be used in funding a private savings or checking account set up by an individual to cover OOP costs for a known and/or potential risk.

Accordingly, contributions to financial instruments can serve to cover OOP expenses for medical conditions with pre-tax funds that provide a considerable savings benefit to individuals who use such accounts. In addition, these financial accounts can serve as an investment vehicle that helps an individual to grow pre-tax dollars to further cover OOP expenses. However, such accounts are oftentimes viewed by individuals as complex insurance products because identifying and establishing what contributions to make to these accounts to optimize their benefits can be daunting and unmanageable. This can be especially true since individuals are required to not only consider current medical conditions in setting contributions to optimize their benefits, but are also required to consider potential (e.g., unknown) medical conditions that can lead to OOP expenses in the future. As a result, many individuals oftentimes heavily discount the future or fail to recognize the substitutability between healthcare and other goods from such account savings.

To further compound this problem, recent studies have shown there is a lack of tools available to assist individuals in the decision making process with respect to making contributions to financial instruments used to cover OOP medical expenses. Determining a contribution rate is a highly complex task that involves not only planning for medical expenses expected to be incurred due to known medical conditions, but also planning for medical expenses that are not yet known and may be incurred due to medical conditions an individual develops in the future. Thus, the setting of a contribution rate for such a financial instrument can be viewed as a fluid process that typically needs to be adjusted as an individual's current health state changes in order for the individual to realize the full benefits of the instrument. However, most individuals do not have the capacity and attention needed to adequately manage this fluid process.

Accordingly, various embodiments are configured to monitor an individual's behaviors (e.g., physiological conditions, purchases of items such as food, and the like) through common personal Internet of things (IoT) data and other sources and determine how those incremental behaviors may contribute to a medical cost in the future. Specifically, various embodiments may involve smart systems designed to evaluate the individual's IoT information, as well as information from other sources such as credit card purchases, to identify behaviors of interest. When a behavior is identified as being performed by the individual that is associated with a risk, a pattern of the behavior may then be evaluated to determine how much financial impact such behavior may have on future health costs for the individual. As a result, embodiments involve automatically adjusting a contribution rate to some type of financial instrument (e.g., an HSA) to compensate for the calculated future health costs.

Thus, various embodiments described herein can facilitate increased monetary contributions to a financial instrument without human intervention as an individual takes part in certain behaviors (e.g., takes certain actions or purchases certain items) in his or her day-to-day routine that may contribute to future medical expenses. In particular, artificial intelligence (AI) is utilized in various embodiments to identify behavioral trends (e.g., habits) that may lead to the individual developing a medical condition. When a behavioral trend is detected suggesting the individual is likely to exceed his or her balance in a financial instrument, embodiments can prompt the individual to increase his or her contribution rate to the account, or facilitate adjusting the contribution rate automatically. In particular embodiments, AI is used in calculating required contribution amounts based on risk factors and associated health costs of medical conditions caused by, or contributed to, the individual's patterns of behaviors over time.

Accordingly, various embodiments of the disclosure may provide the advantages of promoting good health by automatically tracking an individual's behaviors (e.g., habits) against a set of clinically-determined risk factors and increasing the individual's awareness of the effects of the individual's behaviors. Further, various embodiments facilitate the growth of the individual's financial instrument used in covering OOP medical expenses to compensate for bad behaviors (e.g., habits) and/or reward the individual with increased invested account benefits. Thus, various embodiments may optimize the individual's contributions to closely align with predicted annual healthcare costs for the individual. Further, such optimization is accomplished in particular embodiments through the use of automation without human intervention to relieve individuals of the burden of deciding what contributions to make to financial instruments used in covering OOP medical expenses.

Therefore, the disclosed solution provided herein is more effective, efficient, timely, accurate, and faster in optimizing contributions to a financial instrument used in covering OOP medical expenses than if performed by a human. Further, the incorporation of AI through the use of machine learning model(s) can carry out complex mathematical operations that cannot be performed by the human mind (e.g., predicting behavior response and determining contributions to a financial instrument). Especially when such operations need to be performed in a short timeframe that allows for an individual's recent behavior and resulting risk factors from such behavior to be considered in setting a contribution rate for a financial instrument. In doing so, various embodiments of the present disclosure make major technical contributions to improving the efficiency and reliability to optimizing contributions to financial instruments used in covering OOP medical expenses.

Overview of Various Embodiments

Various embodiments of the present disclosure involve performing predictive behavioral response solutions that can be used to generate adjustment models that reward or penalize end users for particular behavioral patterns. An example application of these concepts as they relate to a contribution adjustment is discussed below.

There are several known phenotypic risks associated with humans generally. For example, it is commonly known that obesity in humans can lead to many health conditions such as hypertension, type 2 diabetes, dyslipidemia, cancer, heart disease, liver disease, etc. However, an individual's genetic makeup can also contribute to the level/magnitude/degree of a risk factor with respect to the individual. For example, an individual may be more prone to develop type 2 diabetes due to the individual's genetic traits. Therefore, obesity for such an individual may be a greater risk factor than for other individuals who do not have a type 2 diabetes predisposition. Furthermore, an individual's current health state can contribute to the individual's level of risk with respect to developing a medical condition. For example, an individual who is currently overweight can have a higher risk of becoming obese and thus, developing type 2 diabetes. Accordingly, various embodiments of the disclosure involve the use of artificial intelligence (AI) that takes into consideration both phenotypic risks and an end user's patterns of behavior, current health state, health history, and genotypic risks in identifying potential medical conditions (e.g., issues) and associated costs for the end user and adjusting a current contribution rate to a financial instrument (e.g., an HSA) being used by the end user to cover OOP medical expenses accordingly.

A variety of risk factors may be identified that are considered important with respect to tracking in relation to end users. For instance, such risk factors may be identified and deemed important for tracking purposes because they are known to contribute significantly to medical conditions and/or healthcare costs. For example, type 2 diabetes is known as a leading contributor to healthcare costs in the World. The American Diabetes Association estimated that the cost of diabetes in the United States in 2017 was $327 billion. Individuals with diabetes often spend $16,750 per year on medical expenses with more than half of that ($9,600) directly related to diabetes. These direct expenses include medical supplies, doctor's visits, hospital care, and prescription medications. Therefore, risk factors such as obesity that can lead to type 2 diabetes may be identified as important for tracking purposes in relation to end users.

Accordingly, in various embodiments, instruments such as clinical prediction rules (CPRs) can be used in identifying various risk factors of importance for tracking purposes. Clinical prediction rules are used to estimate the probabilities of clinical conditions or future outcomes by considering a small number of highly valid indicators. In other words, such rules may be used to "rule in" or "rule out" a medical condition (issue) for a patient. Such rules are typically rigorously developed, validated, and evaluated before becoming commonly used in the medical field. Therefore, such rules can oftentimes be considered quite reliable in identifying what risks factors go into predicting a particular medical condition a patient may currently have (diagnostic CPRs) or may develop in the future (prognostic CPRs). Thus, in the example, a prognostic CPR for type 2 diabetes may identify obesity as a highly valid indicator for this medical condition. Accordingly, the risk factors identified through the evaluation of such rules can be used in training a medical conditions prediction machine learning modeling to identify medical conditions an end user may be likely to develop based on the end user's current health state.

With that said, embodiments of the disclosure may also involve the development of one or more clinical risk rule data objects for each of the identified risk factors. Accordingly, in particular embodiments, each clinical risk rule data object defines a threshold that can be used in training a risk generation machine learning model to identify when an end user's pattern of a particular behavior may contribute to a risk factor. For example, a clinical risk rule data object may define the amount of sugar that if consumed by an individual over a specific period of time can lead to obesity. In many instances, such numbers have been established by medical experts.

For instance, medical experts have indicated that an individual should not consume more than thirty grams of sugar a day. Here, a clinical risk rule data object may be defined that identifies an amount of sugar that if consumed over a time period (e.g., three months) can lead to obesity (e.g., clinical risk rule data object for obesity=consuming 2,700 grams of sugar over a three-month period). In addition, the clinical risk rule data object may be defined for a continuous time period to discount an individual's short-term behavior.

For example, an individual who eats a candy bar each day over a three day period is not likely going to amount to the individual becoming obese. However, an individual who eats a candy bar each day over a one month period may be trending towards obesity. Therefore, as discussed in greater detail herein, the threshold established for a clinical risk rule data object can provide a mechanism to identify when an end user is trending towards a risk factor that can lead to a medical condition (issue). That is to say, a clinical risk rule data object may be configured to identify when an end user is developing a risky habit.

Clinical risk rule data objects may also be established for reducing risk factors in various embodiments. For example, a clinical risk rule data object may define an amount of exercise needed to reduce and/or maintain an end user's current weight and thus reduce the end user's chance of becoming obese. In addition, clinical risk rule data objects may be established in particular embodiments that account for an end user's current health state. For example, a first clinical risk rule data object may be defined with respect to sugar consumption and obesity for end users who are currently at an ideal weight, a second clinical risk rule data object for end users who are currently moderately overweight, and a third clinical risk rule data object for end users who are currently highly overweight and/or obese. Accordingly, each of these data objects may define a different threshold that may be applied based on the end user's current weight.

Finally, clinical risk rule data objects may be combined in some embodiments to form compound risk rule data objects as they relate to a common risk factor. For instance, the clinical risk rule data object defining a threshold for sugar consumption with regard to obesity may be combined with the clinical risk rule data object defining a threshold for exercise with regard to obesity. Here, the two data objects may be weighted with respect to their importance in contributing to obesity when used in determining whether an end user is trending towards obesity. Thus, a risk generation machine learning model may be trained on such compound risk rule data objects to recognize a combination of behaviors that can contribute to a risk factor. Those of ordinary skill in the art can envision other configurations of the clinical risk rule data objects in light of this disclosure.

FIG. 1 provides a diagram 100 demonstrating the relationships between behaviors, risk factors, and medical conditions. Here, Behavior A 110 is sleeping, Behavior B 115 is exercising, and Behavior C 120 is consuming sugar. Each of these behaviors has been found to contribute to the risk factor 125 of an individual becoming obese. In addition, the diagram 100 illustrates obesity can contribute to an end user developing several different medical conditions such as Medical Condition A 130 of type 2 diabetes and Medical Condition X 135 of heart disease. Therefore, a risk factor may contribute to more than one medical condition.

Accordingly, a clinical risk rule data object may be defined in various embodiments with respect to each of the identified behaviors and corresponding risk factor. For example, Clinical Risk Rule Data Object A 145 may be defined that averaging less than 7 hours of sleep a day over a month can lead to obesity. In addition, the recommended amount of daily exercise to prevent weight gain is 60 minutes. Therefore, Clinical Risk Rule Data Object B 150 may be defined that averaging less than 60 minutes of exercise each day over a month can lead to obesity. As previously noted, Clinical Risk Rule Data Object C 155 may be defined that consuming 2,700 grams of sugar over a three-month period can lead to obesity. Here, a compound risk rule data object for developing obesity could be defined by combining the three different risk rule data objects.

As further demonstrated in FIG. 1, a behavior can contribute to multiple risk factors and/or medical conditions. Here, Behavior C 120 related to consuming sugar also contributes to Medical Condition Z 140 of a cavity. Accordingly, a second clinical risk rule data object can be developed with respect to this medical condition. For example, Clinical Risk Rule Data Object D 160 may be defined that consuming 3,000 grams of sugar over a three-month period can lead to a cavity. Here, a behavior can result directly into a medical condition without any intervening risk factors. In other words, in the example, the medical condition (Medical Condition Z 140 of developing a cavity), itself, can be viewed as both a condition and a risk factor.

Figure 2:
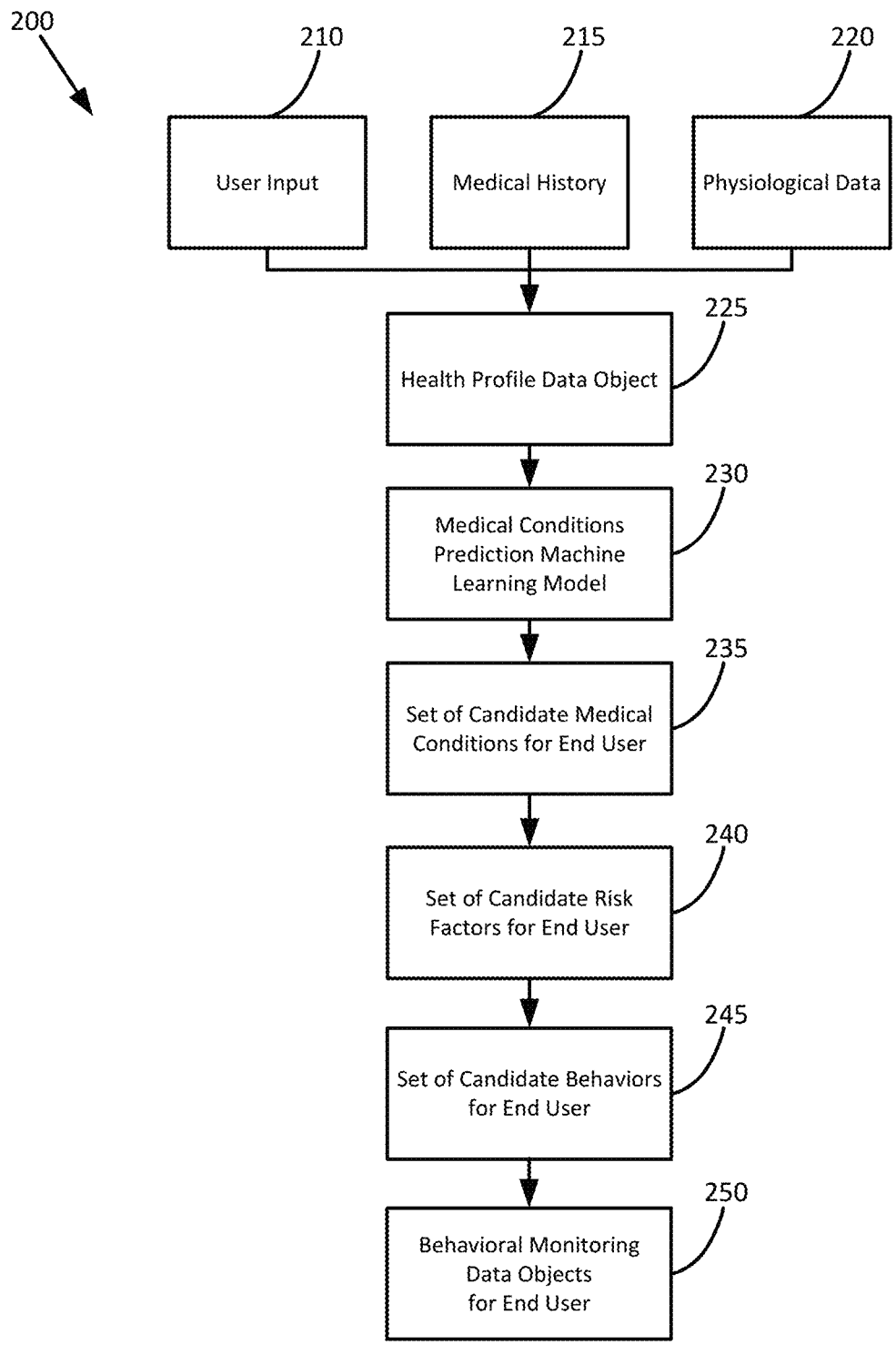
FIG. 2 is an overview of a setup process in accordance with various embodiments of the present disclosure.

Turning now to FIG. 2, an overview 200 is provided with respect to setting up the monitoring of behaviors for an end user according to various embodiments of disclosure. As previously noted, an end user's current health state, as well as genetic makeup, can contribute to the level/magnitude/degree of a risk factor with respect to the end user. Therefore, various embodiments of the disclosure involve the use of a health profile data object 225 that represents an end user's current health state at any given time. The term "current health state" is used throughout the remainder of the disclosure although it should be understood that additional data such as genetic profile, medical history, family medical history, and the like are incorporated into this term. Therefore, the health profile data object 225 for an end user is configured to represent his or her current health state that encompasses both current health, predispositions to medical conditions, health history, and the like.

In particular embodiments, an end user may initially fill out a health questionnaire at the beginning of the process that asks the end user questions on his or her current health, as well as past health. For example, the questionnaire may ask the end user what his or her current height and weight are. The questionnaire may ask the end user if he or her currently has high blood pressure and/or has experienced high blood pressure in the past. In addition, the health questionnaire may ask the end user about his or her family's health history. Further, the questionnaire may inquire about certain behaviors the end user may regularly participate in. For example, the questionnaire may ask the end user if he or she regularly exercises and if so, what types of exercise (e.g., cycling) the end user participates in. Here, the health questionnaire may help to establish the end user's current health, historical health, predisposition to certain health conditions, behavioral habits, and the like. Once monitoring of the end user has begun, further input 210 may be provided by the end user. For instance, the end user may be asked to routinely update his or her medical information (e.g., asked to routinely update his or her weight).

The end user's medical history 215 may also provide information used in particular embodiments in developing the end user's health profile data object 225. Here, medical records may be obtained directly from the end user's healthcare providers and/or the end user's electronic medical records (EMR). In addition, the end user's medical history 215 may include clinical input provided by medical personnel who review the end user's records, as well as a whole genome sequence and/or standard interpretation of predefined risk alleles.

Finally, physiological data 220 may also provide information used in particular embodiments in developing the end user's health profile data object 225. As discussed further herein, one or more devices may be used to monitor various physiological conditions of the end user. For example, the end user may wear a fitness tracker that measures physiological conditions such as the end user's heart rate and/or physical activity (e.g., steps taken over a time period). Accordingly, such information may be provided as further input information used in developing the end user's health profile data object 225.

Thus, the end user's health profile data object 225 represents an overall picture of the end user's current health state and can be used in various embodiments in identifying current and potential medical conditions and associated risk factors. For instance, as detailed further herein, the end user's health profile data object 225 can be used as input to a medical conditions prediction machine learning model 230 configured to identify a set of potential medical conditions (issues) that may be applicable to the individual.

Accordingly, in particular embodiments, the medical conditions prediction machine learning model 230 is configured to process the end user's health profile data object 225 to generate a medical conditions model for the end user. In some embodiments, the medical conditions prediction machine learning model 230 may be configured as a rule-based machine learning model that is configured to infer medical conditions the end user may be likely to develop based on the end user's health profile data object 225 and identified risk factors associated with the medical conditions. Further, the medical conditions prediction machine learning model 230 may be trained using past historical end user data across many end users that includes health profile data objects 225 and known medical conditions for the end users.

Thus, the medical conditions model for the end user may describe a set of medical condition scores for a group of defined medical conditions where each medical condition score describes a likelihood of the end user developing the medical condition corresponding to the score. That is to say, the medical condition score for a particular medical condition provides a probability of the end user developing the medical condition. For instance, in particular embodiments, the medical conditions model may be a data structure such as a vector or a tensor of values in which each value represents a medical condition score for a corresponding medical condition and those medical conditions with a value exceeding a threshold may be identified as applicable to the particular end user.

The set of candidate medical conditions 235 identified from the medical conditions model for the end user can then be used in various embodiments to identify a set of candidate risk factors 240 for the end user. Accordingly, the set of candidate risk factors 240 includes those risk factors known to contribute to the set of candidate medical conditions 235. For example, if the set of candidate medical conditions 235 includes the medical condition type 2 diabetes, then the set of candidate risk factors 240 may include the risk factor obesity.

The set of candidate risk factors 240 can then be used in various embodiments to identify a set of candidate behaviors 245 to monitor for the end user. Thus, the set of candidate behaviors 245 to be monitored for the end user includes those behaviors that lead to the risks factors contributing to development of the medical conditions found in set of candidate medical conditions 235 (that is, those risk factors found in the set of candidate risk factors 240). For instance, a risk factor that contributes to an individual developing type 2 diabetes is obesity. A behavior that can lead to obesity is consumption of sugar. Therefore, a candidate behavior found in the set of candidate behaviors 245 for the end user may include the behavior of consuming sugar.

It is noted that in particular embodiments behaviors related to some medical conditions and/or risk factors may be monitored regardless of the end user because such conditions and/or risk factors are known to be applicable to almost every human. For example, most humans are susceptible to cavities. Therefore, a clinical risk rule data object may be defined by setting out a threshold for consuming sugar that can lead to a cavity and every individual who is monitored may have his or her sugar consumption (behavior) monitored with respect to the potential of developing a cavity. While in other embodiments, behaviors for every medical condition and/or risk factor may be monitored for all end users regardless of their propensity to develop the medical condition.

Finally, a set of behavioral monitoring data objects 250 may be identified for the end user. The set of behavioral monitoring data objects 250 represents the different behavioral monitoring data objects that are to be gathered during the monitoring of the end user. The gathered behavioral monitoring data objects are then used to identify behaviors the end user is participating and/or has participated in during a particular time interval. Therefore, the set of behavioral monitoring data objects 250 are those data objects that can be used to detect the behaviors found in the set of candidate behaviors 245 for the end user. For example, an end user eating a food item such as a donut contributes to the behavior of consuming sugar. Therefore, a behavioral monitoring data object that may be included in the end user's set of behavioral monitoring data objects 250 is monitoring of credit card purchases, which may identify a purchase made by the end user at a donut shop.

It is noted that the setup process described in FIG. 2 can be re-run in various embodiments from time to time after monitoring of the end user has begun. This may be done to update the medical conditions (e.g., the set of candidate medical conditions 235), risk factors (e.g., set of candidate risk factors 240), behaviors (e.g., set of candidate behaviors 245), and behavioral monitoring data objects (e.g., set of behavioral monitoring data objects 250) for the end user. Therefore, as the end user's current health state and behavioral habits change over time, these parameters can be updated to reflect such.

Thus, various embodiments of the disclosure involve monitoring the end user's behaviors to assist in making decisions with respect to adjusting a contribution rate for a financial instrument being used by the end user to pay OOP medical expenses. Accordingly, monitoring the end user may involve a number of different distributed behavior monitoring devices providing a number of different behavioral monitoring data objects. For instance, the end user's purchases may be collected and monitored to identify behaviors that can contribute to certain risk factors. Here, the end user's purchases may be gathered from various sources such as the end user's credit card and/or banking institutions. Accordingly, in particular embodiments, a predictive data analysis system involved in the monitoring process may be in communication with the credit card and/or banking institutions' systems over some type of network such as the Internet so that such information can be collected automatically and in some instances, in real time.

In addition, monitoring of the end user's location and proximity to various items may be performed to identify certain behaviors. For instance, the end user's location may indicate he or she is currently at the gym or a grocery store. Here, GPI information may be monitored on the end user's mobile device to identify his or her location and communicated to the predictive data analysis system. In addition, other mechanisms may be used in monitoring the end user's location and proximity to items. For instance, beacons, computer vision, and other types of location monitoring technology may be used to locate the end user within a location (e.g., within a grocery). For example, beacon identifiers may indicate the end user is located in a sweets aisle at a grocery store. In some instances, the exact item the end user has removed from a shelf may be identified via technology such as RFID proximity detectors and cameras. All such information may be gathered by the predictive data analysis system and used in one or more decision making processes.

Further, monitoring of the end user's physiological conditions may be performed. For instance, the end user may be wearing a smartwatch, fitness tracker, and/or the like that allows monitoring of the end user's heart rate, stress level, movements (engagements in physical activity), etc. Other types of monitoring devices may be used such as a heart rate monitor, blood pressure monitor, and the like. Furthermore, other monitoring may be performed such as, for example, monitoring of medical events (e.g., doctor's visits, dentist visits, emergency room/urgent care visits, medical insurance claims, and the like), monitoring of information manually entered by the end user such as the end user scanning receipts from purchases, and/or monitoring of an electronic calendar found on the end user's mobile device to identified scheduled events. All of which can be gathered and used by the predictive data analysis system in one or more decision making processes. Those of ordinary skill in the art can envision multiple mechanisms (e.g., distributed behavior monitoring devices and behavioral monitoring data objects) that can be used in various embodiment to monitor the end user in light of this disclosure.

Accordingly, in some embodiments, a software application (e.g., an app) may be installed on the end user's mobile device to facilitate the predictive data analysis system's monitoring of the end user. In these particular embodiments, the software application may be configured to gather behavioral monitoring data objects from various distributed behavioral monitoring devices such as the mobile device, itself, and/or other devices in communication with the mobile device for monitoring purposes. For example, the end user may be wearing a fitness tracker that communicates with the mobile device over Bluetooth. The mobile device may communicate with the predictive data analysis system over some type of network such as the Internet, wireless network, cellular network, or the like to facilitate the system's gathering of the behavioral monitoring data objects.

In addition, the software application may facilitate communication with the end user to provide information related to the end user's behaviors and/or effects of such behaviors on certain medical conditions. For example, a message may be provided to the end user via the software application informing the end user of the effect of purchasing and consuming a sugary food item (e.g., a donut) will have on the end user's sugar intake upon detecting the end user has or is about to purchase the sugary food item. In particular instances, the information may further indicate whether the behavior may lead to a change (or suggest a change) in the current contribution rate to the end user's financial instrument. Thus, monitoring the end user may be performed in real time or after the fact for a particular behavior based on the behavioral monitoring data objects being monitored and/or the source of the data objects, as well as communicating information to the end user may be performed in real time or after the fact with respect to performance of a particular behavior. Further, the software application may be configured in some embodiments to confirm whether or not the end user is currently or has participated in a particular behavior. For example, the software application may confirm with the end user whether or not a particular item was purchased.

Figure 3:
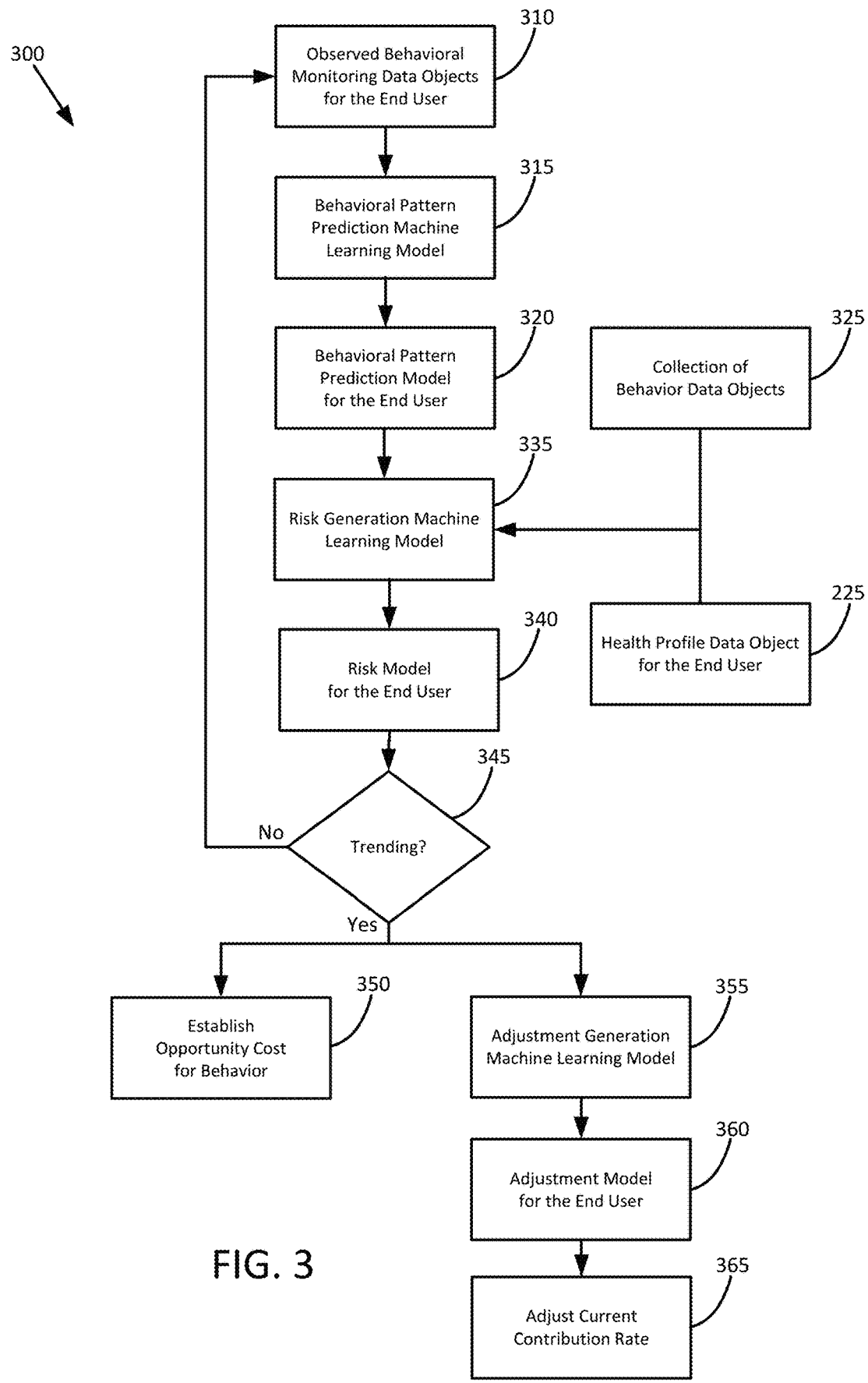
FIG. 3 is an overview of a behavioral monitoring process in accordance with various embodiments of the present disclosure.

Turning now to FIG. 3, an overview 300 is provided with respect to monitoring the behaviors of an end user according to various embodiments of disclosure. The process begins with the predictive data analysis system receiving observed behavioral monitoring data objects 310 associated with the end user from a group of distributed behavioral monitoring devices. Accordingly, the predictive data analysis system processes the one or more behavioral monitoring data objects 310 using a behavioral pattern prediction machine learning model 315 in particular embodiments to generate a behavioral pattern prediction model 320 for the end user. In some embodiments, the behavioral pattern prediction machine learning model 315 is configured to process the one or more behavioral monitoring data objects 310 associated with the end user collected for a particular time interval to generate the behavioral pattern prediction model 320 for the end user with respect to the particular time interval. For example, the behavioral pattern prediction machine learning model 315 may process the behavioral monitoring data objects that include purchases receipts, location (e.g., GPS) information, and calendar event information collected for the end user during a one-hour window of the day.

Accordingly, in particular embodiments, the behavioral pattern prediction machine learning model 315 may be a rule-based machine learning model configured to infer performance of particular behaviors by the end user based on defined patterns of behavioral monitoring data objects. For example, the behavioral pattern prediction machine learning model 315 may be configured to infer that the end user has consumed ice cream as a result of the end user being detected via one or more particular behavioral monitoring data objects 310 in a predefined vicinity of an ice cream store. As another example, the behavioral pattern prediction machine learning model 315 may determine the end user is running when a particular pattern of behavioral monitoring data objects 310 indicates an above-threshold velocity of end user movement patterns.

In some embodiments, the behavioral pattern prediction machine learning model 315 may be a trained machine learning model that is configured to process the one or more behavioral monitoring data objects 310 for the end user collected for a particular time interval to detect one or more behavioral patterns of the end user during the particular time interval. For example, the trained machine learning model may be configured, in part, to process one or more behavioral monitoring data objects 310 associated with the end user collected for a particular time interval to generate a prediction about whether the end user is/was running during the particular time interval. In some embodiments, the behavioral pattern prediction machine learning model 315 may be configured to process, in addition to behavioral monitoring data objects 310 associated with the end user during a particular time interval, data describing defined/detected habits of the particular end user in order to generate the behavioral pattern prediction model 320 for the end user during the particular time interval.

Accordingly, the behavioral pattern prediction model 320 in various embodiments defines properties associated with occurrence or non-occurrence of the set of candidate behaviors 245 for the end user. Specifically, in particular embodiments, the behavioral pattern prediction model 320 is a data structure such as a vector or a tensor that defines properties associated with occurrence or non-occurrence of the set of candidate behaviors 245. For example, the set of candidate behaviors 245 may include a calorie intake event, a running event, a prescription intake event, a water intake event, and a sleep event. Therefore, in this example, the behavioral pattern prediction model 320 may be a data structure such as a vector or a tensor that includes: (i) a first value that describes occurrence/non-occurrence of the calorie intake event with respect to the end user during the particular time interval; (ii) a second value that describes occurrence/non-occurrence of the running event with respect to the end user during the particular time interval; (iii) a third value that describes occurrence/non-occurrence of the prescription intake event with respect to the end user during the particular time interval; (iv) a fourth value that describes occurrence/non-occurrence of the water intake event with respect to the end user during the particular time interval; and (v) a fifth value that describes occurrence/non-occurrence of the sleep event with respect to the end user during the particular time interval.

In some embodiments, the predictive data analysis system may confirm an inferred behavior identified in the behavioral pattern prediction model 320 with the end user—e.g. with a prompt to his or phone: "Are you about to purchase donuts at Krispy Kreme? Yes/No" Accordingly, the behavioral pattern prediction machine learning model 315 may have identified the occurrence of the behavior in the behavioral pattern prediction model 320 based on a data object 310 such as geometric proximity to the store along with data objects 310 showing weekly or daily purchases at the store (e.g., a habit of making purchases at the store).

At this point, various embodiments of the disclosure involve determining the effects of the behaviors shown to have occurred in the behavioral pattern prediction model 320 on the end user's associated risk factor(s). For example, various embodiments involve determining the effects of purchasing and consuming a sugary food item (e.g., a donut) has on the end user becoming obese. Here, the predictive data analysis system in particular embodiments is not configured to necessarily correlate a specific instance of a behavior (e.g., consumption of a donut) to a change in a risk factor (e.g., becoming obese) but instead determine a pattern of the behavior (e.g., pattern of consuming sugary food items) and the effect of the pattern on the risk factor.

Therefore, in various embodiments, the predictive data analysis system is configured to conduct an analysis on the behaviors identified to have occurred to determine whether the individual is trending towards one or more associated risk factors for the behaviors. Accordingly, a collection of behavior data object 325 for each behavior may be used in this analysis. A collection of behavior data object 325 for a particular behavior represents each instance the end user has engaged in the behavior over a past time period. For example, the collection of behavior data object 325 may represent each instance in which the end user has consumed a sugary food item over the past three months. The representation may be in the form of some type of measurement. For example, the collection of behavior data object 325 may identify the number of grams of sugar the end user has consumed over the past three months. In addition, the measurement may be provided with respect to each instance or with respect to some other indicator such as month, week, or day. In some instances, the time period may be set based on one or more corresponding clinical risk rule data object(s). For instance, the three-month window may be based on the corresponding clinical risk rule data object defining an end user is at risk of becoming obese if he or she consumes 2,700 grams of sugar over a three-month period.

In various embodiments, the predictive data analysis system processes the collection of behavior data objects 325 and/or health profile data object 225 for the end user using a risk generation machine learning model 335 to generate a risk model 340 for the end user. Accordingly, in particular embodiments, the risk model 340 may be a data structure such as a vector or a tensor including a group of values, where each value in the group may describe a per-risk factor score for a corresponding risk factor in the set of candidate risk factors 240 for the end user. Each of the per-risk factor scores describes an estimated magnitude of the effect of one or more patterns of behavior exhibited by the end user on a corresponding risk factor.

In some embodiments, the risk generation machine learning model 335 is configured to generate a general risk model for the collection of behavioral objects 325, generate an individual risk model for the collection of behavioral objects 325 in relation to the end user, and combine the general risk model and the individual risk model to generate the risk model 340. Thus, in these particular embodiments, the generated risk model 340 may be based on both phenotype risk data and genetic risk data (e.g., risk data describing established risk alleles for a particular condition) found in the end user's health profile data object 225, thus resulting in a personalized risk prediction mechanism from well-established, existing clinical, nutritional, and other relevant data. Other information that may be used from the end user's health profile data object 225 may include, for example, the end user's demographics such as age and weight, geographic location at which the end user resides, current health conditions, behavioral habits, and the like. Thus, the per-risk factor scores found in the risk model 340 may indicate which of the risk factors found in the set of candidate risk factors 240 are trending for the end user.

At this point, the predictive data analysis system may determine 345 whether any risk factors are trending for the end user. If so, then the predictive data analysis system may establish in particular embodiments how much (e.g., an opportunity cost) the detected behaviors associated with the trending risk factors contribute to healthcare costs for the end user 350. Accordingly, in particular embodiments, the predictive data analysis system determines the opportunity cost for a particular behavior by dividing an OOP cost for the trending risk factor by the threshold for a corresponding clinical risk rule data object for the behavior.

For example, the risk model 340 for the end user may identify a trending risk factor for the end user is obesity. Here, the behavioral pattern prediction model 320 for the end user may indicate an occurrence of the consumption of a sugary food item. In this instance, the sugary food item may have been a donut (as determined from a purchase receipt). The grams of sugar in the donut may be determined to be eleven grams based on the ingredients found in the donut. Many manufacturers and/or agencies make such information publicly available through various sources such as the Internet. If such specific information is not readily available for the donut, than an assumed amount of sugar (e.g., average amount of sugar) may be used. The corresponding clinical risk rule data object for the consumption of a sugary food item leading to obesity may be 2,700 grams of sugar over a three-month period. So in the example, if the OOP cost for an individual becoming obese averages $435 a year, then the cost for consuming one gram of sugar is $435/2,700=$0.16. Thus, the predictive data analysis system determines the opportunity cost for consuming the donut is $1.76.

In some embodiments, the OOP cost may be based on one or more potential medical conditions the end user may have a likelihood of developing based on the risk factor. For example, the end user may have a likelihood of developing type 2 diabetes (as identified in his or her set of candidate medical conditions 235). Therefore, the system may use $435 as the OOP cost based on covering yearly expenses related to developing type 2 diabetes. OOP costs of various medical conditions may be stored in some type of data structure such as a table in a database that is accessible by the predictive data analysis system.

Further, depending on the circumstances, the OOP cost may be based on group data and/or individual data. For instance, if no historical data is available for the end user then group data may be relied on to calculate an average for the OOP cost. However, if individual data is available, then the predictive data analysis system may be configured to use such data to skew the group average. For example, if the end user has had three consecutive years of trending towards obesity and has not yet developed type 2 diabetes, then the system may adjust the OOP cost accordingly.

In some embodiments, the predictive data analysis system may communicate the opportunity cost associated with the detected behavior to the end user. For instance, the system may send a message that is displayed on the software application hosted on the end user's mobile device informing him or her of the result (e.g., consequences) of his or her behavior. For example, the system may send a message that informs the end user "if you complete your purchase of the food item containing high sugar content, you may increase your future health savings account contributions by $1.76." Thus, such communicates can serve as motivation for the end user to avoid certain behaviors that can lead to higher healthcare costs and a higher contribution rate. Likewise, the predictive data analysis system can provide messages with respect to positive behaviors such as, for example, "if you complete your workout, you may reduce your future health savings account contributions by $1.50." Therefore, such communications can also motivate the end user to practice positive behaviors.

At this point, the predictive data analysis system in various embodiments determines whether a change in the individual's current contribution rate should be instituted in light of the potential medical condition(s) that may result from the trending risk factor(s). The predictive data analysis system processes the risk model 340 for the end user using an adjustment generation machine learning model 355 to generate an adjustment model 360 for the user. Accordingly, the adjustment generation machine learning model 355 may be a rule-based machine learning model that includes, for each per-risk factor score defined by a risk model 340, an adjustment value. As a result, the adjustment model 360 describes a required effect of the risk model 340 on a financial instrument for the end user. For example, the adjustment model 360 may require that the contribution to the financial instrument be increased based on the per-risk factor scores described by the risk model 340.

In some embodiments, the adjustment generation machine learning model 355 may comprise a time series prediction model and an adjustment application model. Here, the time series prediction model is configured to determine a projected balance of the end user's financial instrument over a prospective period of time, and the adjustment application model is configured to generate the adjustment model 360 based on the projected balance and the risk model 340. Accordingly, in some embodiments, the time series prediction model is an autoregressive integrated moving average (ARIMA) model. In general, an ARIMA is a statistical analysis model that uses time series data to predict future trends. An ARIMA model allows for the forecasting of a time series, in this case the balance of the user's financial instrument, using the series' past values. Accordingly, the time series prediction model can be weighted by known health conditions of the end user and used to predict future balances expected for the financial instrument.

If the adjustment model 360 indicates the contribution to the end user's financial instrument should be increased, then the predictive data analysis system adjusts the current contribution rate to the end user's financial instrument accordingly 365. The predictive data analysis system initially analyzes a current medical plan data object detailing the end user's current medical plan (e.g., high/low deductible plan, PPO, HMO, co-pays, maximum OOP, etc.) to determine a required contribution amount to cover OOP expenses expected to be incurred due to the potential medical condition(s) that may result from the trending risk factor(s). As detailed further herein, this process is carried out by the predictive data analysis system employing one or more contribution models in particular embodiments to determine what contribution amount is needed to properly fund the individual's financial instrument to adequately cover the OOP expenses that can be expected to be incurred by the end user as a result of the potential medical condition(s) due to the trending risk factor(s).

Here, in particular embodiments, the predictive data analysis system may employ a long-term model to account for potential medical condition(s) that are considered as long-term conditions. Accordingly, the long-term model is configured to optimize contributions over a long time horizon. Therefore, this particular model is generally configured to better account for (fund expenses for) medical conditions that are considered long-term conditions such as, for example, type 2 diabetes. In addition, the predictive data analysis system may employ a short-term model to account for potential medical condition(s) that are considered to be short-term conditions such as, for example, a cavity. The short-term model is configured to cover the OOP maximum expense in each year, subject to any policies associated with the financial instrument (e.g., subject to an annual contribution limit). Therefore, this particular model is generally configured to better account for (fund expenses for) medical conditions that occur in/over a short time period.

In some embodiments, the predictive data analysis system is configured to weight and combine the outputs from both models to account for instances when both potential long-term and short-term medical conditions may develop due to the trending risk factor(s). Here, the system may weight (bias) the outputs from the models based on the potential medical conditions and combine them to generate a provisional contribution amount. The predictive data analysis system may then use this provisional contribution amount to modify a base contribution amount derived from amounts based on the potential medical condition(s) associated with the trending risk factor(s) to determine a required contribution amount to cover the end user's expected OOP expenses. In particular instances, the base contribution amounts may be established based on historical data on expenses associated with the corresponding medical condition(s).

Finally, the predictive data analysis system increments the end user's current contribution rate in light of the required contribution amount. Here, the predictive data analysis system may be configured in some embodiments to reference current legal and/or policy constraints placed on the financial instrument in adjusting the end user's current contribution rate. For example, policy may be in place that prevents frequent changes to the contribution rate. Therefore, the predictive data analysis system may be configured to address the policy by maintaining an internal ledger and then implementing the change within an allowable window (e.g., every two months).

Accordingly, in particular embodiments, the predictive data analysis system is configured to communicate the adjustment to the current contribution rate to the end user. For instance, in particular embodiments, the system may send a message that is displayed via the software application hosted on the end user's mobile device informing him or her of the adjustment. Depending on the embodiment, the end user may be allowed to accept or deny the adjustment to his or her current contribution rate or the adjustment may be implemented automatically. Further details are now provided herein on the predictive data analysis system, AI technologies, and processes involved in implementing various embodiments of the disclosure.

Computer Program Products, Systems, Methods, and Computing Entities

Embodiments of the present disclosure may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of a data structure, apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises a combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially, such that one instruction is retrieved, loaded, and executed at a time. In some exemplary embodiments, retrieval, loading, and/or execution may be performed in parallel, such that multiple instructions are retrieved, loaded, and/or executed together. Thus, such embodiments can produce specifically configured machines performing the steps or operations specified in the block diagrams and flowchart illustrations. Accordingly, the block diagrams and flowchart illustrations support various combinations of embodiments for performing the specified instructions, operations, or steps.

Exemplary System Architectures

Figure 4:
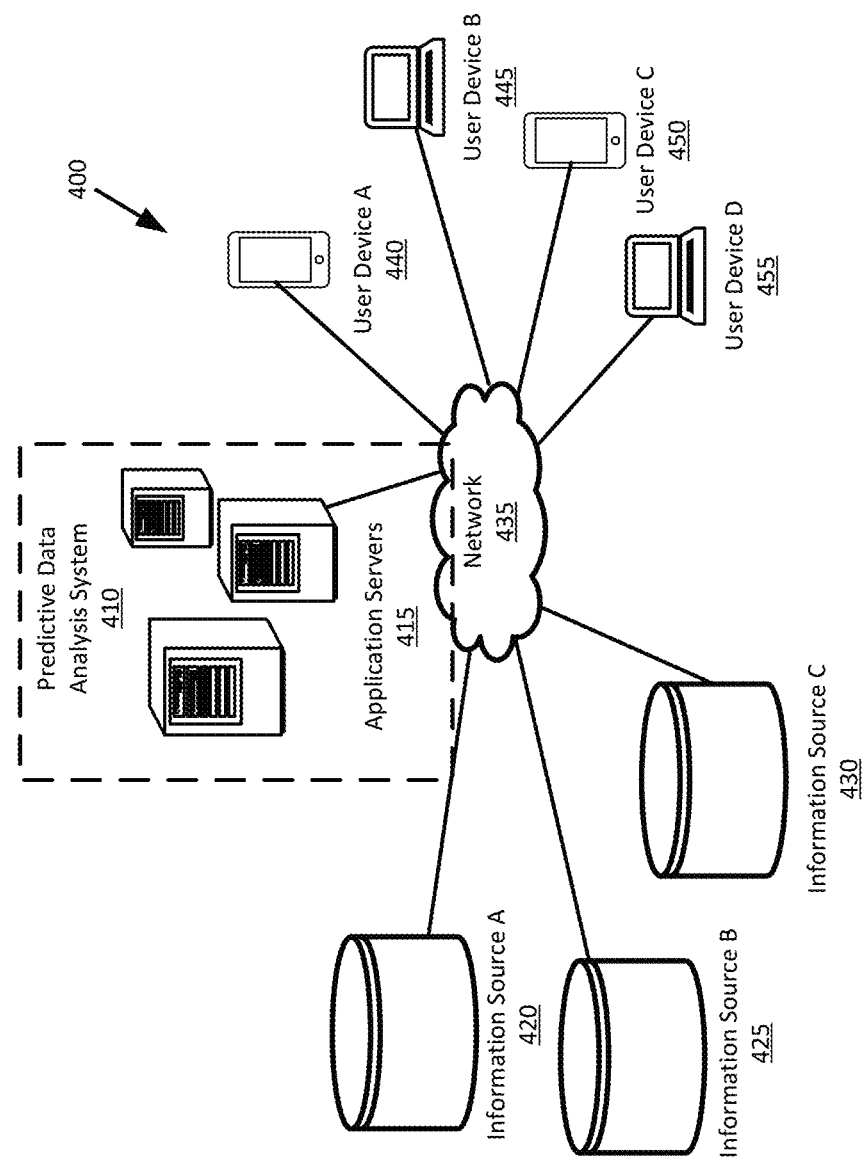
FIG. 4 is a diagram of a system architecture that can be used in conjunction with various embodiments of the present disclosure.

FIG. 4 provides an illustration of a system architecture 400 involving a predictive data analysis system 410 that may be used in accordance with various embodiments of the disclosure. The architecture 400 includes various components involved in gathering information on end users that is then analyzed by the predictive data analysis system 410 to determine whether the end users are trending towards risk factors, and whether contribution rates to financial instruments used by the end users should be adjusted accordingly.

Here, the predictive data analysis system 410 may include one or more application servers 415 that may be in communication with various information sources 420, 425, 430 over one or more networks 435. These various information sources 420, 425, 430 may include, for example, systems for credit card providers, banking institutions, health insurance providers, medical providers, retailers, and the like. In addition, the one or more applications servers 415 may be in communication with various end user devices 440, 445, 450, 455 (e.g., a desktop or laptop computer and/or a mobile device such as a smartphone or tablet). These information sources 420, 425, 430 and end user devices 440, 445, 450, 455 may serve as distributed behavioral monitoring devices providing behavioral monitoring data objects in various embodiments. Accordingly, the application servers 415 may gather information from these sources 420, 425, 430 and devices 440, 445, 450, 455, as well as communicate information to these sources 420, 425, 430 and devices 440, 445, 450, 455.

Accordingly, the application server(s) 415 found within the predictive data analysis system 410 may be made up of several servers, storage media, layers, and/or other components, which may be chained or otherwise configured to interact and/or perform tasks as detailed herein. In addition, the application server(s) 415 may include any appropriate hardware and/or software for interacting with the information sources 420, 425, 430 and end user devices 440, 445, 450, 455 as needed to execute aspects of one or more applications for conducting processes that involve gathering and analyzing information from the sources 420, 425, 430 and devices 440, 445, 450, 455, and handling data access and business logic for such.

As noted, the application server(s) 415, information sources 420, 425, 430 and end user devices 440, 445, 450, 455 may communicate with one another over one or more networks 435. Depending on the embodiment, these networks 435 may comprise any type of known network, such as a land area network (LAN), wireless land area network (WLAN), wide area network (WAN), metropolitan area network (MAN), cellular network, the Internet, etc., or combination thereof. In addition, these networks 435 may comprise any combination of standard communication technologies and protocols. For example, communications may be carried over the networks 435 by link technologies such as Ethernet, 802.11, CDMA, 3G, 4G, or digital subscriber line (DSL). Further, the networks 435 may support a plurality of networking protocols, including the hypertext transfer protocol (HTTP), the transmission control protocol/internet protocol (TCP/IP), or the file transfer protocol (FTP), and the data transferred over the networks 435 may be encrypted using technologies such as, for example, transport layer security (TLS), secure sockets layer (SSL), and internet protocol security (IPsec). Those skilled in the art will recognize FIG. 4 represents but one possible configuration of a system architecture 400, and that variations are possible with respect to the protocols, facilities, components, technologies, and equipment used.

Figure 5:
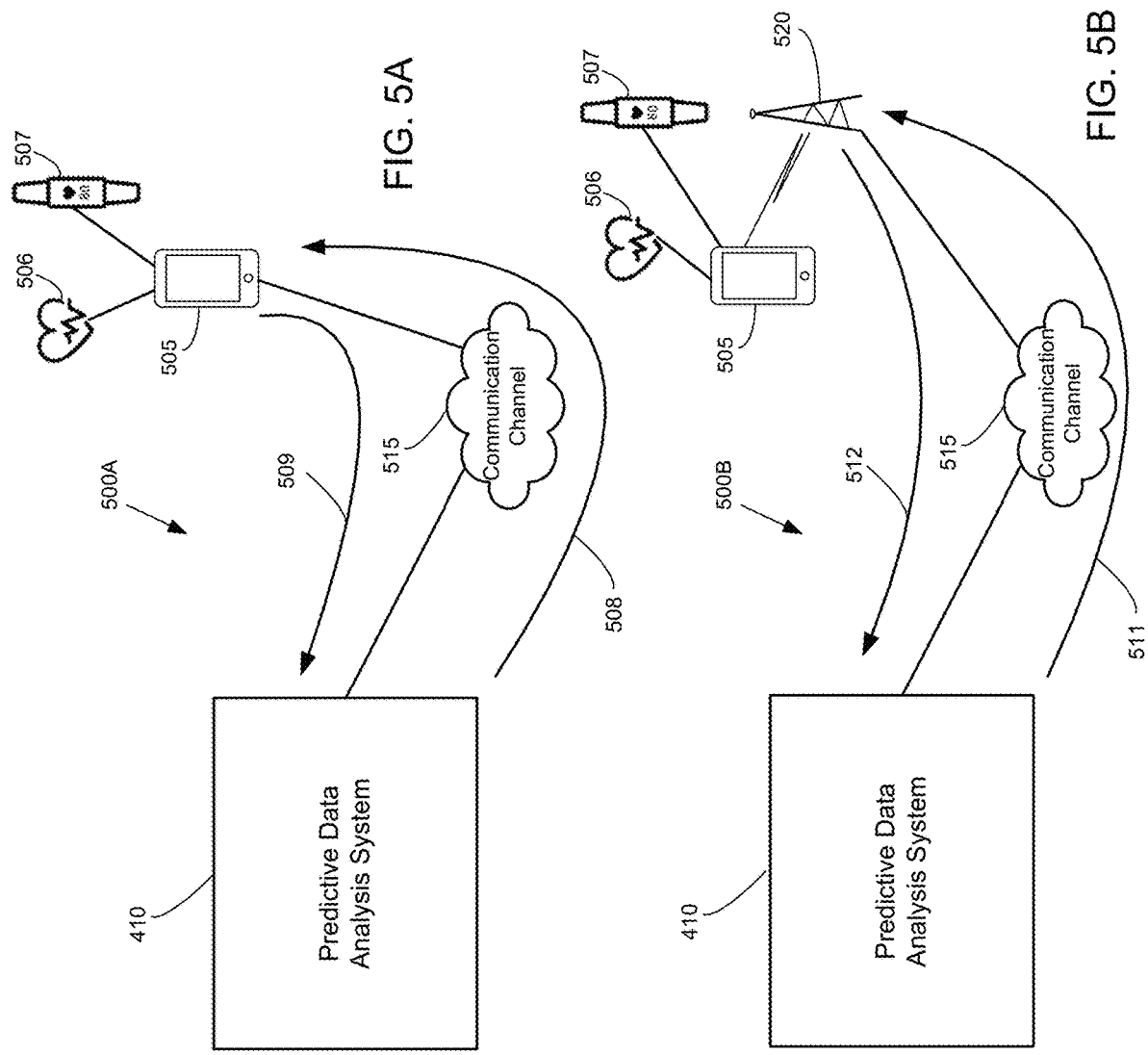
FIGS. 5A-5B are diagrams of architectures employing a mobile device that may be used in conjunction with various embodiments of the present disclosure.

FIGS. 5A and 5B show embodiments of architectures 500A, 500B employing a mobile device that may be used in conjunction with various embodiments of the disclosure. Beginning with FIG. 5A, the architecture 500A in this figure involves the predictive data analysis system 410 directly communicating with an end user's mobile device 505 to obtain information (e.g., behavioral monitoring data objects) on various behaviors involving the end user from the device 505 that can be used in various embodiments. Accordingly, the end user may use one or more other devices such as, for example, a heart rate monitor 506, a fitness tracker 507, and the like to gather information on physiological conditions which can be communicated (e.g., via Bluetooth) to the end user's mobile device 505.

In this particular architecture, the predictive data analysis system 410 communicates over a communication channel 515 directly with the end user's mobile device 505. For example, the communication channel 515 may involve some type of network, such as a land area network (LAN), wireless land area network (WLAN), wide area network (WAN), metropolitan area network (MAN), the Internet, etc. Such communication may be facilitated in particular embodiments via a software application residing on the mobile device 505. Accordingly, this software application may gather the various types of information (e.g., behavioral monitoring data objects) from the different devices such as the mobile device 505 itself and/or from the devices communicating with the mobile device 505, such as the heart rate monitor 506 and fitness tracker 507. While in other embodiments, the mobile device 505 may be configured to provide such functionality without the need of the software application.

Accordingly, the predictive data analysis system 410 communicates information (e.g., messages) 508 to the mobile device 505 over the communication channel 515, as well as the mobile device 505 (e.g., software application residing on the mobile device 505) can gather information involving the end user and communicate such information 509 to the predictive data analysis system 410 over the communication channel 515. As a result, the predictive data analysis system 410 can then use the information 509 provided by the user's mobile device 505 in various embodiments as detailed further herein.

Similarly, the predictive data analysis system 410 in the architecture 500B shown in FIG. 5B communicates with the end user's mobile device 505. However, for this particular architecture 500B, the predictive data analysis system 410 instead sends information 511 to the end user's mobile device 505 via the end user's cellular carrier 520 and the cellular carrier 520 forwards the formation 511 to the mobile device 505. Again, the information 511 sent from the predictive data analysis system 410 to the cellular carrier 520 may be over some type of communication channel 515. For example, the communication channel 515 may involve some type of network, such as a land area network (LAN), wireless land area network (WLAN), wide area network (WAN), metropolitan area network (MAN), the Internet, etc. Further the cellular carrier 520 may receive information 512 from the mobile device 505 that the cellular carrier 520 then provides over the communication channel 515 to the predictive data analysis system 410. As in the case with the first architecture 500A, the predictive data analysis system 410 can then use the information 512 provided by the user's mobile device 505 in various embodiments as detailed further herein.

Exemplary Computing Entity

Figure 6:
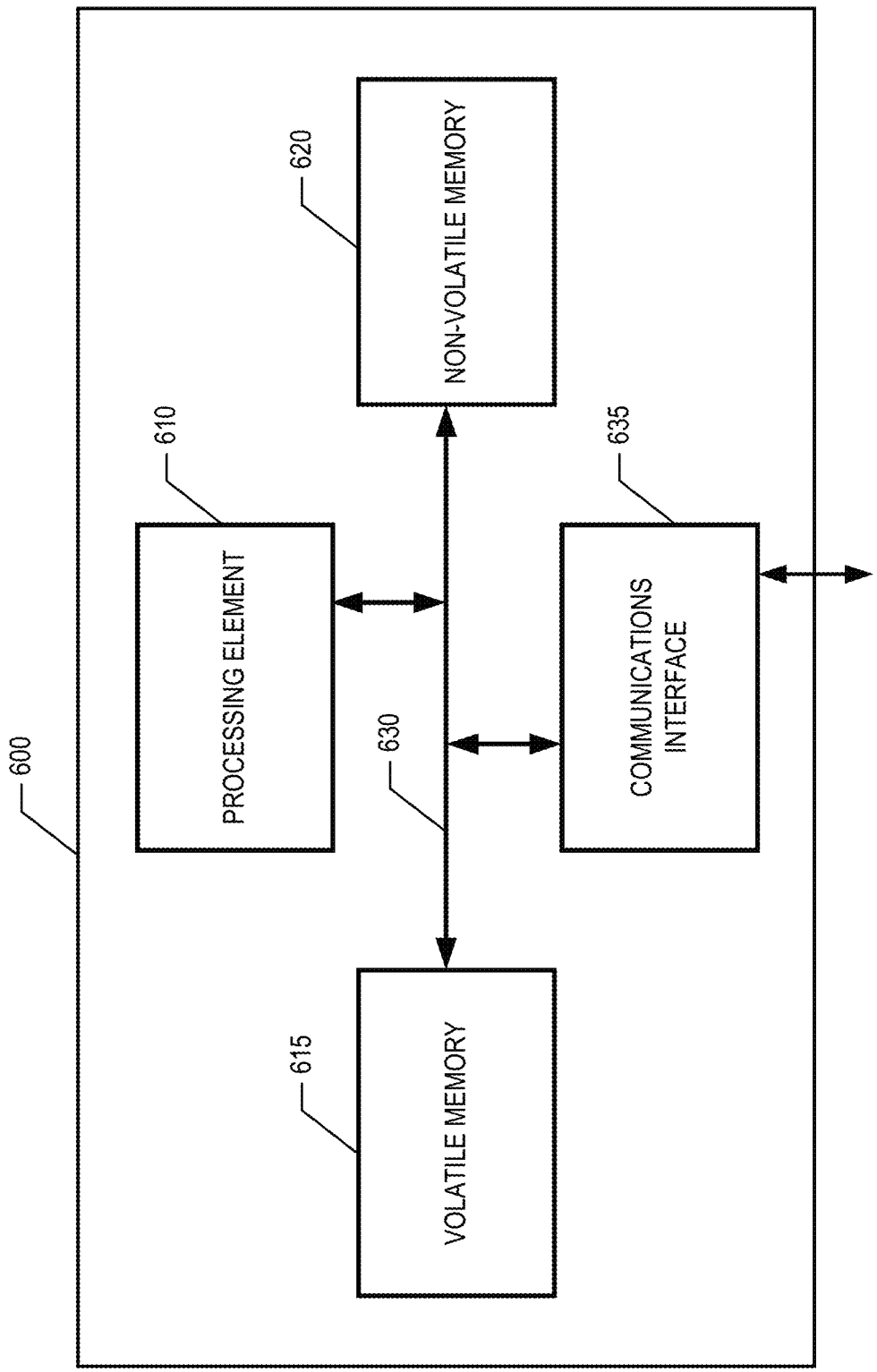
FIG. 6 is a schematic of a computing entity that may be used in conjunction with various embodiments of the present disclosure.

FIG. 6 provides a schematic of a computing entity 600 that may be used in accordance with various embodiments of the present disclosure. For instance, the computing entity 600 may be one or more of the application servers 415 found within the predictive data analysis system 410 previously described in FIG. 4. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

Although illustrated as a single computing entity, those of ordinary skill in the art should appreciate that the computing entity 600 shown in FIG. 6 may be embodied as a plurality of computing entities, tools, and/or the like operating collectively to perform one or more processes, methods, and/or steps. As just one non-limiting example, the computing entity 600 may comprise a plurality of individual data tools, each of which may perform specified tasks and/or processes.

Depending on the embodiment, the computing entity 600 may include one or more network and/or communications interfaces 625 for communicating with various computing entities, such as by communicating data, content, information, and/or similar terms used herein interchangeably that can be transmitted, received, operated on, processed, displayed, stored, and/or the like. Thus, in certain embodiments, the computing entity 600 may be configured to receive data from one or more data sources and/or devices as well as receive data indicative of input, for example, from a device.

The networks used for communicating may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks may have any suitable communication range associated therewith and may include, for example, global networks (e.g., the Internet), MANs, WANs, LANs, or PANs. In addition, the networks may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

Accordingly, such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the computing entity 600 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1X (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The computing entity 600 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

In addition, in various embodiments, the computing entity 600 includes or is in communication with one or more processing elements 610 (also referred to as processors, processing circuitry, and/or similar terms used herein interchangeably) that communicate with other elements within the computing entity 600 via a bus 630, for example, or network connection. As will be understood, the processing element 610 may be embodied in several different ways. For example, the processing element 610 may be embodied as one or more complex programmable logic devices (CPLDs), microprocessors, multi-core processors, coprocessing entities, application-specific instruction-set processors (ASIPs), and/or controllers. Further, the processing element 610 may be embodied as one or more other processing devices or circuitry. The term circuitry may refer to an entirely hardware embodiment or a combination of hardware and computer program products. Thus, the processing element 610 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 610 may be configured for a particular use or configured to execute instructions stored in volatile or non-volatile media or otherwise accessible to the processing element 610. As such, whether configured by hardware, computer program products, or a combination thereof, the processing element 610 may be capable of performing steps or operations according to embodiments of the present disclosure when configured accordingly.

In various embodiments, the computing entity 600 may include or be in communication with non-volatile media (also referred to as non-volatile storage, memory, memory storage, memory circuitry and/or similar terms used herein interchangeably). For instance, the non-volatile storage or memory may include one or more non-volatile storage or memory media 620, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media 620 may store files, databases, database instances, database management system entities, images, data, applications, programs, program modules, scripts, source code, object code, byte code, compiled code, interpreted code, machine code, executable instructions, and/or the like. The term database, database instance, database management system entity, and/or similar terms used herein interchangeably and, in a general sense, to refer to a structured or unstructured collection of information/data that is stored in a computer-readable storage medium.

In particular embodiments, the memory media 620 may also be embodied as a data storage device or devices, as a separate database server or servers, or as a combination of data storage devices and separate database servers. Further, in some embodiments, the memory media 620 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. As already discussed, various embodiments contemplated herein communicate with various information sources and/or devices in which some or all the information/data required for various embodiments of the disclosure may be stored.

In various embodiments, the computing entity 600 may further include or be in communication with volatile media (also referred to as volatile storage, memory, memory storage, memory circuitry and/or similar terms used herein interchangeably). For instance, the volatile storage or memory may also include one or more volatile storage or memory media 615 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media 615 may be used to store at least portions of the databases, database instances, database management system entities, data, images, applications, programs, program modules, scripts, source code, object code, byte code, compiled code, interpreted code, machine code, executable instructions, and/or the like being executed by, for example, the processing element 610. Thus, the databases, database instances, database management system entities, data, images, applications, programs, program modules, scripts, source code, object code, byte code, compiled code, interpreted code, machine code, executable instructions, and/or the like may be used to control certain aspects of the operation of the computing entity 600 with the assistance of the processing element 610 and operating system.

As will be appreciated, one or more of the computing entity's components may be located remotely from other computing entity components, such as in a distributed system. Furthermore, one or more of the components may be aggregated and additional components performing functions described herein may be included in the computing entity 600. Thus, the computing entity 600 can be adapted to accommodate a variety of needs and circumstances.

Exemplary Mobile Computing Entity

Figure 7:
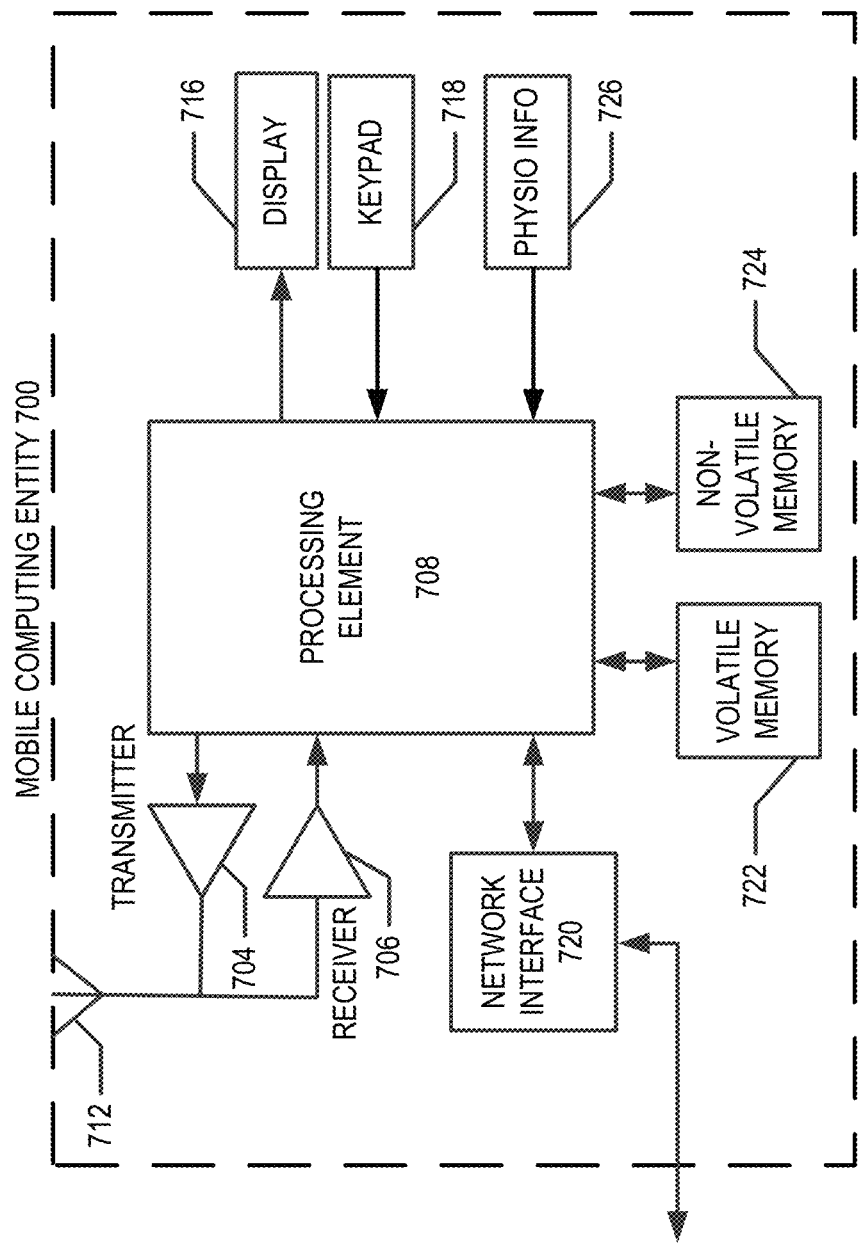
FIG. 7 is a schematic of a mobile computing entity that may be used in conjunction with various embodiments of the present disclosure.

FIG. 7 provides an illustrative schematic representative of a mobile computing entity 700 that can be used in conjunction with embodiments of the present disclosure. For example, the mobile computing entity may be the mobile device 505 as discussed in FIGS. 5A and 5B. Accordingly, in various embodiments, the mobile computing entity 700 may be any mobile device such as a smartphone, tablet, computing device, and/or the like that may be in communication with one or more physiological monitoring components/elements 726 (e.g., hearth rate monitor 506, fitness tracker 507, etc.) that are configured to gather physiological data on an end user of the entity 700 such as, for example, heart rate, blood pressure, breathing rate, stress level, movement from activity, and the like and provide the physiological data thereof.

As shown in FIG. 7, the mobile computing entity 700 can include an antenna 712, a transmitter 704 (e.g., radio), a receiver 706 (e.g., radio), and a processing element 708 that provides signals to and receives signals from the transmitter 704 and receiver 706, respectively. The signals provided to and received from the transmitter 704 and the receiver 706, respectively, may include signaling information/data in accordance with an air interface standard of applicable wireless systems to communicate with various entities, such as the predictive data analysis system 410 and/or the like. In an example embodiment, the transmitter 704 and/or receiver 706 are configured to communicate via one or more SRC protocols. For example, the transmitter 704 and/or receiver

706 may be configured to transmit and/or receive information/data, transmissions, and/or the like of at least one of Bluetooth protocols, low energy Bluetooth protocols, NFC protocols, RFID protocols, IR protocols, Wi-Fi protocols, ZigBee protocols, Z-Wave protocols, 6LoWPAN protocols, and/or other short range communication protocol. In various embodiments, the antenna 712, transmitter 704, and receiver 706 may be configured to communicate via one or more long range protocols, such as GPRS, UMTS, CDMA200, 1xRTT, WCDMA, GSM, EDGE, TD-SCDMA, LTE, E-UTRAN, EVDO, HSPA, HSDPA, Wi-Fi, Wi-Fi Direct, WiMAX, and/or the like.

In this regard, the mobile computing entity 700 may be capable of operating with one or more air interface standards, communication protocols, modulation types, and access types. More particularly, the mobile computing entity 700 may operate in accordance with any of a number of wireless communication standards and protocols. In a particular embodiment, the mobile computing entity 700 may operate in accordance with multiple wireless communication standards and protocols, such as GPRS, UMTS, CDMA200, 1xRTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the mobile computing entity 700 can communicate with various other devices using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The mobile computing entity 700 can also download changes, add-ons, and updates, for instance, to its firmware, software (e.g., including executable instructions, applications, program modules), and operating system.

According to one embodiment, the mobile computing entity 700 may include location determining aspects, devices, modules, functionalities, and/or similar words used herein interchangeably. For example, the mobile computing entity 700 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the mobile computing entity's 700 position in connection with a variety of other systems, including cellular towers, Wi-Fi access points, and/or the like. Similarly, the mobile computing entity 700 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE transmitters, NFC transmitters, and/or the like. These indoor positioning aspects can be used in a variety of settings to determine the location of someone or something to within inches or centimeters.

The mobile computing entity 700 may also comprise a user interface device comprising one or more user input/output interfaces (e.g., a display 716 and/or speaker/speaker driver coupled to a processing element 708 and a touch screen, keyboard, mouse, and/or microphone coupled to a processing element 708). For example, the user interface may be configured to provide an application, browser, interactive user interface, dashboard, webpage, and/or similar words used herein interchangeably executing on and/or accessible via the mobile computing entity 700 to cause display or audible presentation of information/data and for user interaction therewith via one or more user input interfaces.

In one embodiment, the functionality described herein (and user interface) may be provided as a software application (e.g., an app) executing on the mobile computing entity 700. In such an implementation, the software application may be integrated with a variety of other software applications executing on the mobile computing entity 700 to gather information from the other applications. Moreover, the user interface can comprise or be in communication with any of a number of devices allowing the mobile computing entity 700 to receive data, such as a keypad 718 (hard or soft), a touch display, voice/speech or motion interfaces, scanners, readers, or other input device. In embodiments including a keypad 718, the keypad 718 can include (or cause display of) the conventional numeric (0-9) and related keys (#, *), and other keys used for operating the mobile computing entity 700 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs, the mobile computing entity 700 can capture, collect, store information/data, user interaction/input, and/or the like.

The mobile computing entity 700 can also include volatile storage or memory 722 and/or non-volatile storage or memory 724, which can be embedded and/or may be removable. For example, the non-volatile storage or memory 724 may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile storage or memory 722 may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory 722, 724 can store databases, database instances, database management system entities, data, applications, programs, program modules, scripts, source code, object code, byte code, compiled code, interpreted code, machine code, executable instructions, and/or the like to implement the functions of the mobile computing entity 700.

Exemplary System Operations

The logical operations described herein may be implemented (1) as a sequence of computer implemented acts or one or more program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These states, operations, structural devices, acts, and modules may be implemented in software, in firmware, in special purpose digital logic, and any combination thereof. Greater or fewer operations may be performed than shown in the figures and described herein. These operations may also be performed in a different order than those described herein.

Mobile Setup Module

Figure 8:
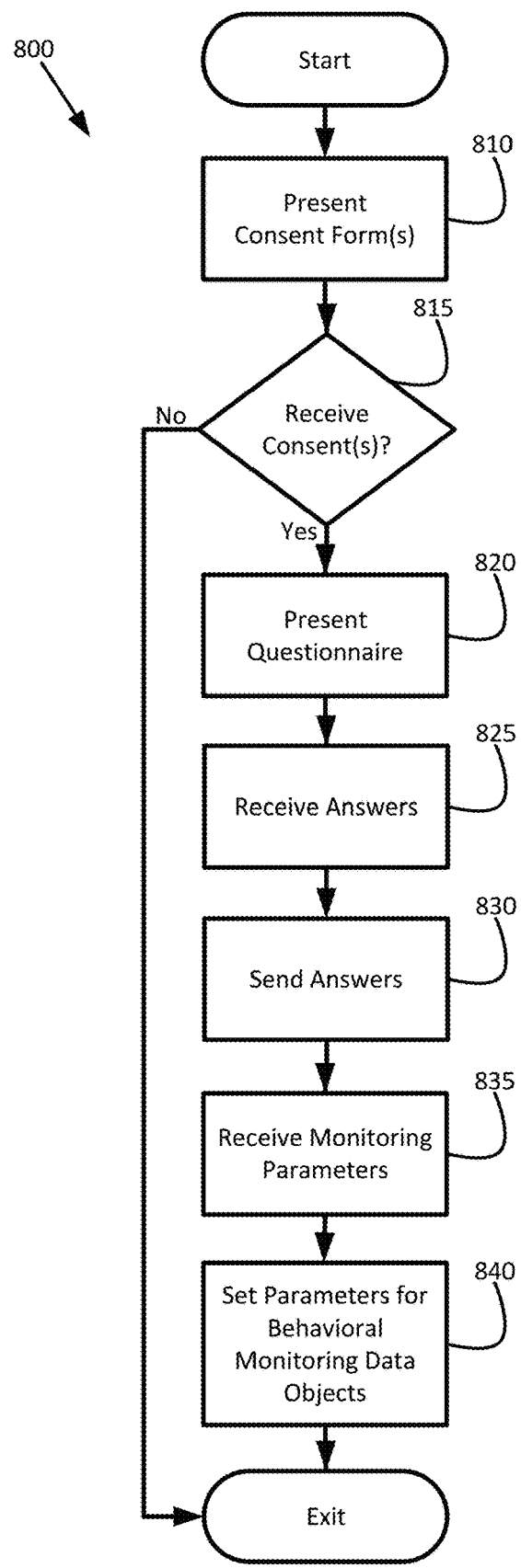
FIG. 8 is a process flow for setting up monitoring on a mobile device in accordance with various embodiments of the present disclosure.

Turning now to FIG. 8, additional details are provided regarding a process flow for setting up the monitoring of an end user using a mobile device 505 according to various embodiments. FIG. 8 is a flow diagram showing a mobile setup module for performing such functionality according to various embodiments of the disclosure. Here, the mobile setup module may be a module found within a software application (e.g., an "app") residing on the mobile device 505 used by the end user. Accordingly, the mobile device 505 may be a device such as a smartphone, tablet, smartwatch, laptop, and/or the like.

As previously noted, embodiments of the disclosure involve monitoring behaviors of the end user with respect to the behaviors' contribution to various risk factors. Accordingly, such monitoring may be performed via the end user's mobile device 505, was well as receiving behavioral monitoring data objects from other sources. In some instances, such sources may require the end user's consent to obtain such data objects. For example, consent is often needed to access an individual's medical records. Therefore, the process flow 800 begins in various embodiments with the mobile setup module presenting one or more consent forms to the end user to gain access to various information needed in monitoring the end user in Operation 810. Depending on the embodiment, a single form may be provided or multiple forms may be provided with respect to different sources of information. For example, a first consent form may be provided with respect to gaining access to the end user's credit card purchases from the end user's credit card provider, while a second consent form may be provided with respect to gaining access to the end user's medical records. Those of ordinary skill in the art can envision multiple types of consents that may be asked of the end user to gain access to various information in light of this disclosure.

Accordingly, each consent form is presented to the end user on his or her mobile device 505 along with a mechanism to provide consent (e.g., a button), and the end user indicates whether he or she consents to having the corresponding information (e.g., behavioral monitoring data objects) monitored. Thus, in some embodiments, the end user can pick and choose what types of behaviors can be monitored based on whether or not the end user provides consent to access the behavioral monitoring data objects needed to monitor a certain type of behavior. In addition, other types of consent can be requested of the end user such as, for example, whether the current contribution rate set for a financial instrument for the end user can be automatically adjusted based on the monitoring of his or her behavior. In some instances, certain consents may be required by the end user to have his or her behaviors monitored. Therefore, the mobile setup module determines whether it has received the appropriate consent(s) from the end user in Operation 815.

If the appropriate consent(s) has been provided, then the mobile setup module provides the end user with a health questionnaire in Operation 820. As previously discussed, a health profile data object 225 may be constructed for the end user that represents the end user's current health state. Therefore, the questionnaire may ask the end user questions on his or her current health, as well as on past health. For example, the questionnaire may ask the end user his or her current height, weight, blood pressure, cholesterol levels, and the like. In addition, the questionnaire may ask the end user about his or her medical history, as well as his or her family's medical history. In some instances, the questionnaire may be configured to actually gather health information on the end user. For example, the questionnaire can be configured to read the end user's current heart rate by using some monitoring device in communication with the mobile setup module. Further, the questionnaire may ask the end user about specific behaviors and/or habits associated with behaviors. Thus, the health questionnaire may help to establish the end user's current health, historical health, predisposition to certain health conditions, and/or behavioral habits.

Accordingly, the mobile setup module receives the answers to the health questionnaire in Operation 825 and sends the answers to the predictive data analysis system 410 in Operation 830. The predictive data analysis system 410 receives the answers and uses the answers as one source of information in constructing the end user's health profile data object 225. As previously noted, in particular embodiments, the predictive data analysis system 410 may use information found in the end user's health profile data object 225 once it has been constructed as input to a medical conditions prediction machine learning model 230 to identify a set of candidate medical conditions 235 for the end user.

For example, the medical conditions prediction machine learning model 230 may indicate based on information found in the end user's health profile data object 225 that the user is likely to develop type 2 diabetes. Therefore, in these particular embodiments, one or more behaviors that contribute to risks leading to type 2 diabetes may be identified as behaviors to be monitored for the end user such as, for example, consuming sugary food items that can contribute to developing obesity. While in other embodiments, a set number of behaviors, regardless of the end user, may be monitored for all end users or a combination of both may be monitored.

Therefore, the mobile setup module may receive one or more monitoring parameters in Operation 835. These monitoring parameters may indicate various behavioral monitoring data objects that are to be gathered for the end user during the monitoring process that are used to identify relevant behaviors. For example, a relevant behavior for the end user may be the user engaging in physical activity (e.g., exercising). Therefore, a behavioral monitoring data object that may be gathered for the end user is motion/movement detected using some type of device such as a fitness tracker 507 that is in communication with the mobile device 505. Thus, in Operation 840, the mobile setup module may set the monitoring parameters needed to gather motion/movement data detected by the fitness tracker 507. Once the mobile setup module has completed setting the monitoring parameters needed to gather the behavioral monitoring data objects for the relevant behaviors, the process for monitoring the end user's behaviors using the mobile device 505 can begin.

Monitoring Setup Module

Figure 9:
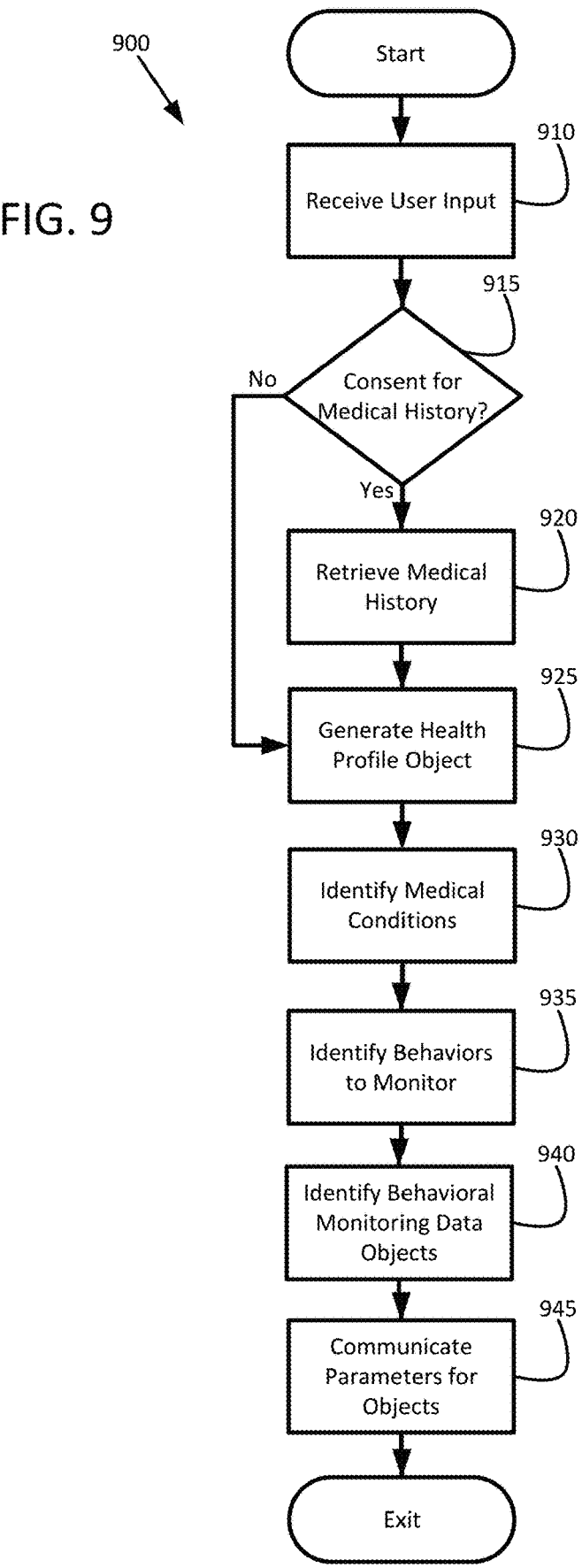
FIG. 9 is a process flow for setting up the monitoring of an end user in accordance with various embodiments of the present disclosure.

Turning now to FIG. 9, additional details are provided regarding a process flow for setting up the monitoring of an end user by the predictive data analysis system 410 according to various embodiments. FIG. 9 is a flow diagram showing a monitoring setup module for performing such functionality according to various embodiments of the disclosure. Specifically, the monitoring setup module may be used in setting up the monitoring of the end user's behaviors remotely by the predictive data analysis system 410.

The process flow 900 begins in various embodiments with the monitoring setup module receiving user input 210 in Operation 910. As previously discussed, an end user who may wish to begin having his or her behaviors monitored may engage in a setup process that involves gathering information from the end user through the use of an instrument such as a questionnaire. The questionnaire may gather information on the end user with respect to the end user's current health state, as well as behavioral habits.

In addition, the user input 210 may include consent(s) provided by the end user to allow monitoring of his or her behaviors, as well as consent(s) to gather information on the end user from various sources such as credit card providers, financial institutions, medical providers, wireless carrier providers, and the like. Therefore, the monitoring setup module determines whether consent to access the end user's medical records has been provided by the user in Operation 915.

If so, then the monitoring setup module retrieves the end user's medical records in Operation 920. As previously discussed, the end user's medical records may be obtained from various healthcare providers and/or health insurance providers for the end user, as well as the end user's EMR. Accordingly, the monitoring setup module may be configured to electronically retrieve the end user's medical records from various systems associated with the providers. Here, the monitoring setup module may use the end user's consent in gaining access to such information. In other instances, the monitoring setup module may be configured to initiate a process to gain access to the end user's medical records if such access cannot be gained immediately. For example, the monitoring setup module may initiate a request for a particular healthcare provider to gain access to the end user's health records held by the provider. Those of ordinary skill in the art can envision multiple mechanisms that can be employed in various embodiments to retrieve the end user's medical records in light of this disclosure.

At this point, the monitoring setup module generates the health profile data object 225 for the end user in Operation 925. As already discussed, the health profile data object 225 provides the end user's current health state and behavioral habits. Therefore, in various embodiments, the monitoring setup module uses the user input 210 and medical history 215 (e.g., medical records) in constructing the health profile data object 225 for the end user. It is noted that the health profile data object 225 may be updated from time to time in some embodiments based on updated information provided by the end user and/or updated medical information on the end user. For example, if the medical records for a healthcare provider may not be available during the initial setup process for the end user, then the health profile data object 225 for the end user may be updated once the medical records have been received. Further, the end user's health profile data object 225 may be updated based on physiological data gathered on the end user during monitoring, such as weight, blood pressure, heart rate, and the like.

In particular embodiments, the monitoring setup module may be configured to initially identify a set of candidate medical conditions 235 that are applicable to the end user in Operation 930. This operation is performed in these particular embodiments so that a set of candidate risk factors 240 associated with the set of candidate medical conditions 235 can be identified so that the behaviors corresponding to the set of candidate risk factors 240 can be monitored. This can allow monitoring of the end user to be fine-tuned so that the more important behaviors the end user may participate in that could contribute to him or her developing a medical condition are monitored. However, with that said, this operation may not be performed in other embodiments, but instead, the same behaviors may be monitored for all end users. Other embodiments may involve a combination of the two in which some of the behaviors monitored for the end user may be based on the set of candidate risk factors 240 identified for the end user, while other behaviors monitored for the end user are those monitored for all end users.

Thus, as previously discussed, the monitoring setup module may employ a medical conditions prediction machine learning model 230 in particular embodiments in identifying the set of candidate medical conditions 235 for the end user. Here, information found within the end user's health profile data object 225 may be provided as input to the model 230 and the model 230 may generate a medical conditions model for the end user where the medical conditions model provides a medical condition score for each medical condition. Accordingly, each medical condition score represents a probability of the end user developing the corresponding medical condition. Thus, the monitoring setup module may identify the set of candidate medical conditions 235 as those medical conditions having a medical condition score exceeding a threshold. Note that the end user and/or end user's medical records may have indicated during information gathering that he or she has already developed certain medical conditions. Accordingly, such information may be detailed in the end user's health profile data object 225 and thus may be provided as input to the model 230.

Once the set of candidate medical conditions 235 have been identified for the end user, the monitoring setup module determines the behaviors to monitor for the end user in Operation 935. As previously discussed, relationships may be established in particular embodiments between various behaviors, risk factors, and medical conditions using medical literature and expertise. As noted, several sources, such as clinical prediction rules, are publicly available that can be used in establishing these relationships. For instance, an example of such relationships was previously discussed with respect to FIG. 1. Therefore, the monitoring setup module may identify the behaviors that should be monitored for the end user by considering such relationships.

For instance, in particular embodiments, the monitoring setup module may identify a set of candidate risk factors 240 for the end user based on these established relationships and the medical conditions found in the set of candidate medical conditions 235. The module may then identify a set of candidate behaviors 245 for the end user based the established relationships and the risk factors found in the set of candidate risk factors 240. Accordingly, the behaviors found in the set of candidate behaviors 245 are the behaviors to be monitored for the end user.

At this point, the monitoring setup module identifies a set of behavioral monitoring data objects 250 used in detecting the behaviors found in the set of candidate behaviors 245 in Operation 940. The monitoring setup module then communicates monitoring parameters for one or more of the set of behavioral monitoring data objects 250 to one or more of the end user's devices in Operation 945. Further, the monitoring setup module may setup the necessary parameters for one or more of the behavioral monitoring data objects that may involve other systems and devices other than those belonging to the end user. As a result, the end user's devices may receive the monitoring parameters and take the necessary steps required to have the behavioral monitoring data objects collected accordingly. At this point, monitoring of the end user's behaviors can begin.

Mobile Monitoring Module

Figure 10:
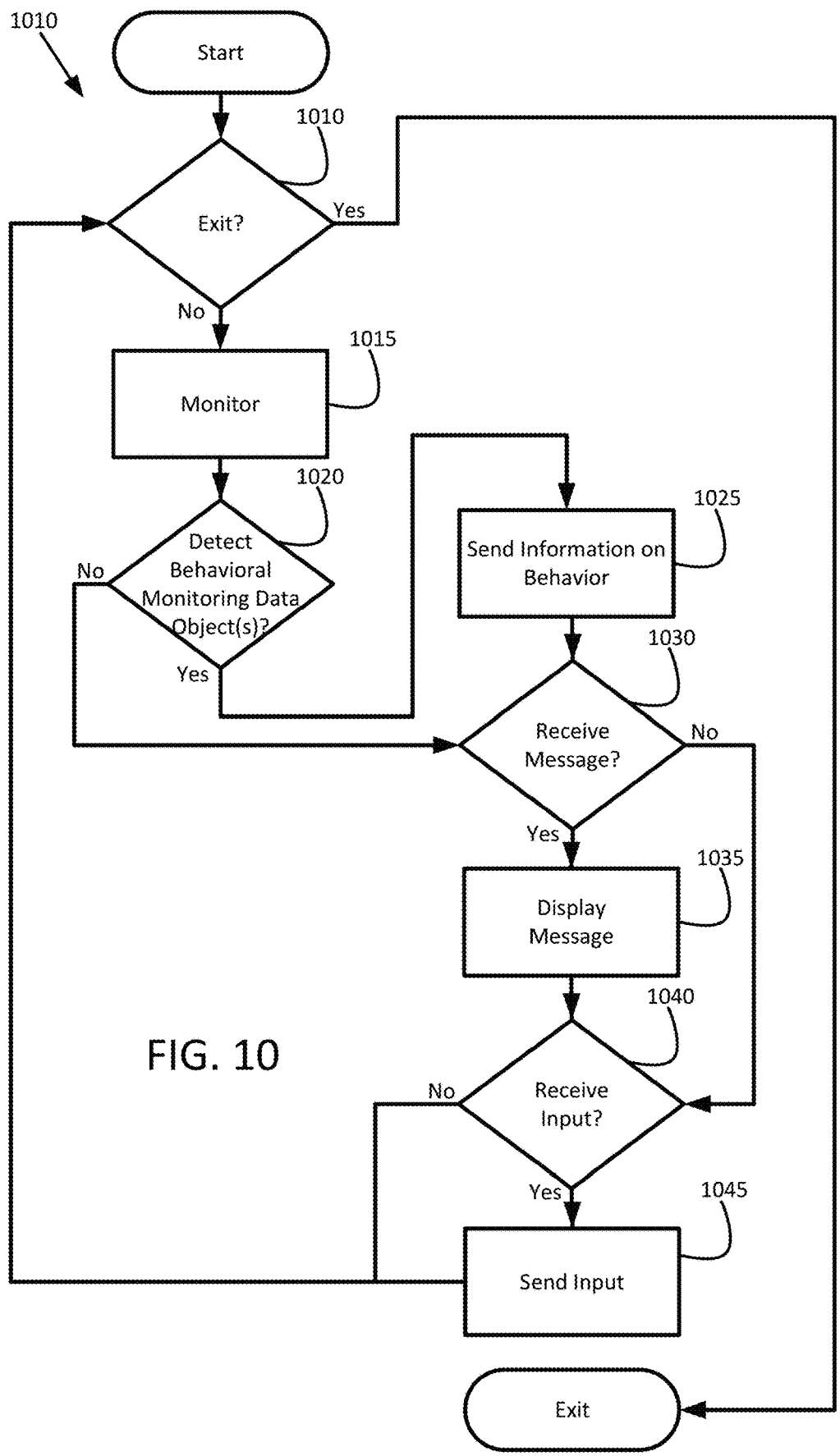
FIG. 10 is a process flow for monitoring behavior using a mobile device in accordance with various embodiments of the present disclosure.

Turning now to FIG. 10, additional details are provided regarding a process flow for gathering behavioral monitoring data objects for an end user using a mobile device 505 according to various embodiments. FIG. 10 is a flow diagram showing a mobile monitoring module for performing such functionality according to various embodiments of the disclosure. Similar to the mobile setup module, the mobile monitoring module may be a module found within a software application (e.g., an "app") residing on the mobile device 505 used by the end user. As discussed below, the mobile monitoring module is configured to receive behavioral monitoring data objects from various sources (e.g., a fitness tracker 507 being worn by the end user) and send the data objects to the predictive data analysis system 410.

The process flow 1000 begins with the mobile monitoring module determining whether to exit in Operation 1010. For instance, the end user may have decided to end the monitoring of his or her behavior and as a result, discontinues use of the mobile monitoring module and/or software application by shutting one and/or the other off. If the mobile monitoring module determines not to exit, then the module begins monitoring in Operation 1015.

Accordingly, the mobile monitoring module may receive behavioral monitoring data objects from various sources such as the mobile device 505, itself, and/or from various monitoring devices in communication with the mobile device 505. In addition, the end user may directly enter a behavioral monitoring data object into the software application. For example, the software application may provide a feature that allows the end user to scan in receipts from purchases. Therefore, the mobile monitoring module may receive behavioral monitoring data objects that may represent several different types of data, such as, for example, physiological data gathered on the end user, purchasing data, location data, event data from the end user's calendar, and the like.

Therefore, the mobile monitoring module determines whether one or more behavioral monitoring data objects has been detected (e.g., communicated) in Operation 1020. If so, then the module sends the behavioral monitoring data object(s) to the predictive data analysis system 410 in Operation 1025. In turn, the predictive data analysis system 410 may identify a behavior associated with the one or more behavioral monitoring data objects and send a message to confirm the behavior with the end user. If this is the case, then the mobile monitoring module may determine whether it has received such a message in Operation 1030, and if so, communicate (e.g., display) the message to the end user in Operation 1035.

Accordingly, the end user may respond to the message (e.g., confirming the behavior) and the mobile monitoring module determines whether it has received the end user's response (e.g., confirmation) in Operation 1040. If so, then the mobile monitoring module sends the response to the predictive data analysis system 410 in Operation 1045. This exchange of messages may continue with respect to the particular behavior. For example, the predictive data analysis system 410 may determine an opportunity cost for the behavior and communicate such to the end user.

Furthermore, the predictive data analysis system 410 and end user may exchange information (e.g., messages) that is not necessarily related to a particular behavior that has been detected. For example, the software application may provide a function that allows the end user to review any adjustments made to his or her current contribution rate due to his or her behaviors over a certain time period. Therefore, in this example, the mobile monitoring module may determine the end user has input a request for such information and as a result, send the request to the predictive data analysis system 410.

Remote Monitoring Module

Figure 11:
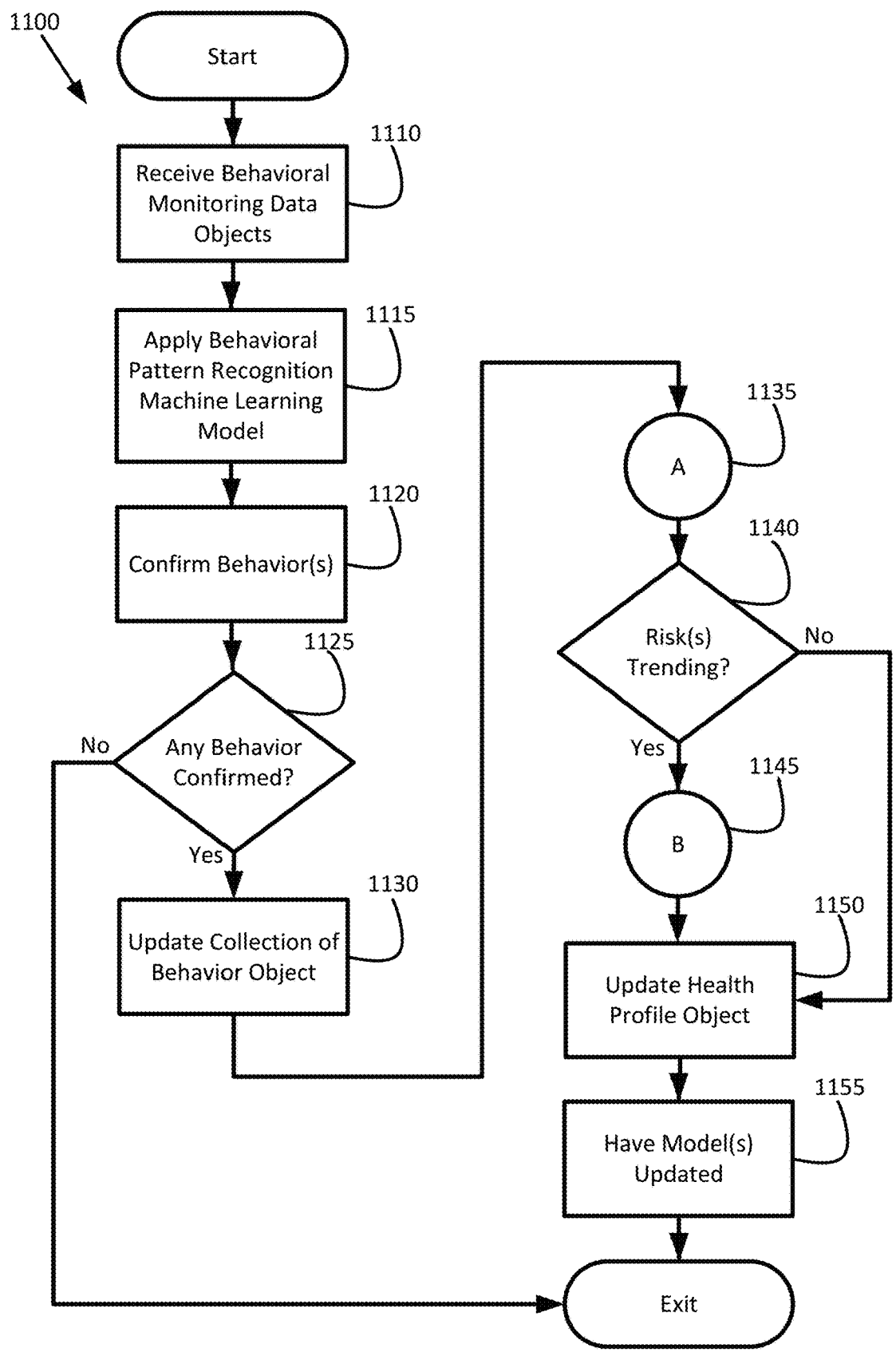
FIG. 11 is a process flow for monitoring behavior of an end user in accordance with various embodiments of the present disclosure.

Turning now to FIG. 11, additional details are provided regarding a process flow for monitoring an end user's behaviors remotely according to various embodiments. FIG. 11 is a flow diagram showing a remote monitoring module for performing such functionality according to various embodiments of the disclosure. For example, the remote monitoring module may be hosted within the predictive data analysis system 410 previously discussed. Here, the predictive data analysis system 410 may invoke the remote monitoring module based on one or more behavioral monitoring data objects received for the end user.

For instance, one or more trigger events may be defined that are used to identify instances when the behavior(s) of the end user should be monitored/identified based on one or more behavioral monitoring data objects that are received for the end user. For example, a behavioral monitoring data object (e.g., GPS data) may be received that indicates the end user is in the proximity of a donut shop. Here, the end user's location may serve as a trigger event to invoke the remote monitoring module. Accordingly, the predictive data analysis system 410 may gather one or more behavioral monitoring data objects that may be related such as, for example, purchasing information gathered for a time interval when the end user is/was detected to be located within the proximity of the donut shop, and invoke the remote monitoring module to analyze the one or more behavioral monitoring data objects. Those of ordinary skill in the art can envision other trigger events that may be defined and used in light of this disclosure.

Therefore, the process flow 1100 begins with the remote monitoring module receiving the one or more behavioral monitoring data objects in Operation 1110. In addition, information may be provided to the remote monitoring module identifying the particular end user. The remote monitoring module then determines whether the end user is/has performed a behavior of interest by processing the one or more behavioral monitoring data objects using the behavioral pattern prediction machine learning model 315 to produce a behavioral pattern prediction model 320 for the end user in Operation 1115. As previously discussed, the behavioral pattern prediction model 320 may provide an occurrence/non-occurrence indicator for each of the behaviors found in the set of candidate behaviors 245 for the end user. For example, the behavioral pattern prediction model 320 may provide an indicator of an occurrence of the end user consuming a sugary food item.

Because the one or more behavioral monitoring data objects that are provided as input to the behavioral pattern prediction machine learning model 315 can involve multiple types of data (e.g., textual, numerical, image, categorical, binary, continuous, and the like), the behavioral pattern prediction machine learning model 315 may be configured in particular embodiments as a multi-input/mixed data model. A multi-input/mixed data model allows for mixed data types to be combined using deep learning approaches. Oftentimes different data types that are to be used as inputs to a machine learning model require separate preprocessing that may involve scaling, normalization, and/or feature engineering. Therefore, a multiple input/mixed data model allows for each data type to be processed independently and used as input to a separate deep learning process. The output(s) for each process can then be concatenated together to produce final output(s) based on the combined processes.

For example, the one or more behavioral monitoring data objects used in identifying occurrences of various behaviors may involve textual, numerical, categorical, and image data. Here, in this example, the behavioral pattern prediction machine learning model 315 may involve one or more multi-layer perception neural networks configured to use the textual, numerical, and categorical data as input and a convolutional neural network configured to use the image data as input. Accordingly, the behavioral pattern prediction machine learning model 315 may involve a neural network having a fully-connected or non-fully-connected classifier using an activation function, such as, for example, linear, leaky ReLU, and/or the like, configured to use the outputs produced by each of the models as inputs. Further, various optimizers such as, for example, Adan, RMSProp, and/or the like, may be used. As a result of such a configuration, the mixed data types found in the various behavioral monitoring data objects can be used in generating the behavioral pattern prediction model 320 for the end user.

In particular embodiments, the remote monitoring module may be configured to confirm the behavior(s) shown to have occurred in the behavioral pattern prediction model 320 with the end user. If this is the case, then the remote monitoring module does so in Operation 1120. For example, this operation may involve the remote monitoring module having a message sent to a device of the end user (e.g., the end user's mobile device 505) and displayed via a software application hosted on the device. The end user may then confirm or deny that he or she is or has participated in the behavior(s).

It should be noted that depending on the circumstances and behavior, the one or more behavioral monitoring data objects used in identify the occurrence of a particular behavior may be received in real time or after the fact in various embodiments. For instance, if the end user is participating in a physical activity (e.g., exercising) and this activity is detected by a fitness tracker 507 being worn by the end user, then a behavioral monitoring data object on the activity may be provided to the remote monitoring module in real time while the end user is participating in the activity. While in other instances, the one or more behavioral monitoring data objects on a particular behavior may be communicated after the fact. For example, the end user may have visited a donut shop and purchased a donut and coffee using his or her credit card. Here, the visit may be detected based on purchasing information received from the end user's credit card provider after the purchase and therefore, the one or more behavioral monitoring data objects or this behavior may be communicated after the behavior has taken place.

If the remote monitoring module determines the end user has confirmed at least one of the behaviors identified to have occurred in the behavioral pattern prediction model 320 in Operation 1125, then the remote monitoring module updates the user's corresponding collection of behavior data object(s) 325 in Operation 1130. Thus, the particular instance of the behavior is added to the corresponding collection data object for each of the behaviors that has occurred. Furthermore, the remote monitoring module may update the behavioral pattern prediction model 320 to reflect the occurrence/non-occurrence of the behaviors based on the end user's confirmation.

Figure 12:
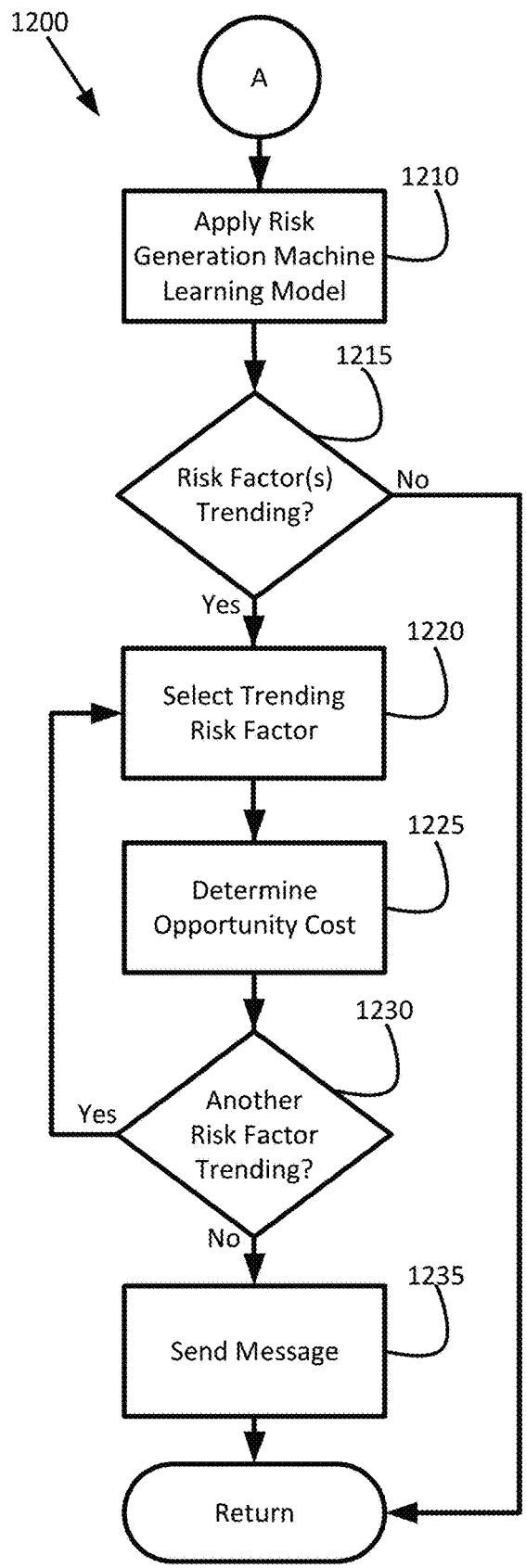
FIG. 12 is a process flow for evaluating risk factor(s) associated with one or more behaviors in accordance with various embodiments of the present disclosure.

At this point, the remote monitoring module determines whether the end user may be trending towards one or more risks factors in Operation 1135. Here, in particular embodiments, the remote monitoring module performs this operation by invoking a risk evaluation module (FIG. 12). As discussed further herein, the risk evaluation module identifies whether the collection of behavior data objects 325 for each of the behaviors identified as occurring indicates the end user is trending toward any of the associated risks factor(s) for the behavior.

Therefore, the remote monitoring module determines whether the end user is trending towards one or more risk factors in Operation 1140. If so, then the module determines whether the end user's current contribution rate made to a financial instrument holding funds used to cover OOP medical expenses should be adjusted in light of the trending risk factor(s) and associated medical condition(s) in Operation 1145. The remote monitoring module performs this operation in various embodiments by invoking a contribution module (FIG. 13) and the contribution module determines whether the end user's current contribution rate should be adjusted based on a required contribution amount to cover OOP expenses expected to be incurred due the medical condition(s) the end user may develop as a result of the trending risk factor(s). As discussed further herein, depending on the embodiment, the end user's current contribution rate may be adjusted automatically based the analysis or the end user may need to approve such an adjustment.

The remote monitoring module then updates the end user's health profile data object 225 based on the trending risk factor(s) in Operation 1150. This operation is performed in various embodiments to ensure the end user's health profile data object 225 is up-to-date and accurately represents the end user's current health state. Finally, the remote monitoring module may also have one or more of the machine learning models 230, 315, 335, 355 updated in some embodiments in Operation 1155.

Continuous learning can be used in machine learning environments to ensure an artificial intelligence deployment is continually updated as new data is collected. Such an implementation can address the limitations of a one-time training of the models 230, 315, 335, 355 and enable the models 230, 315, 335, 355 in various embodiments to continuously update themselves and thus become more accurate in generating predictions. For example, if an end user becomes diagnosed with type 2 diabetes and his or her health profile data object 225 is updated accordingly, then the medical conditions prediction machine learning model 230 can be retrained (updated) based on the end user's updated health profile data object 225 to better identify when this particular medical condition is applicable. Thus, incorporating continuous learning into various embodiments can lead to more accurate models 230, 315, 335, 355.

Risk Evaluation Module

Turning now to FIG. 12, additional details are provided for determining whether an end user is trending towards one or more risk factors based on the end user's participation in one or more behaviors according to various embodiments. FIG. 12 is a flow diagram showing a risk evaluation module for performing such functionality according to various embodiments of the disclosure. As previously mentioned, the risk evaluation module may be invoked by another module in particular embodiments to identify trending risk factors for the end user such as, for example, the remote monitoring module previously described. However, with that said, the risk evaluation module may not necessarily be invoked by another module and may execute as a stand-alone module in other embodiments.

Turning now to FIG. 12, the process flow 1200 begins with the risk evaluation module processing the collection of behavior data objects 325 for the end user and/or the end user's health profile data object 225 using the risk generation machine learning model 335 in Operation 1210. As previously discussed, the risk generation machine learning model 335 in particular embodiments generates a risk model 340 for the end user based on the inputs. Accordingly, the risk model 340 provides a per-risk factor score for each risk factor found in the end user's set of candidate risk factors 240 where the per-risk factor score for a particular risk factor provides an estimated magnitude of the effect of one or more patterns of behavior for the end user on the corresponding risk factor. Accordingly, in particular embodiments, any risk factor to have a per-risk factor score exceeding a threshold is found to be trending.

As previously noted, the risk generation machine learning model 335 may be configured in particular embodiments to generate a general risk model for the collection of behavior data objects 325, generate an individual risk model for the collection of behavior data objects 325 in relation to the end user, and combine the general risk model and the individual risk model to generate the risk model 340. Thus, in these particular embodiments, the generated risk model 340 may be based on both phenotype risk data and genetic risk data (e.g., risk data describing established risk alleles for a particular condition) found in the end user's health profile data object 225. Other information that may be used from the end user's health profile data object 225 may include, for example, the end user's demographics such as age and weight, geographic location with respect to residency, current health conditions, behavioral habits, and the like.

Thus, the risk evaluation module determines whether any of the risk factors are trending for the end user based on the risk model 340 in Operation 1215. If so, then the module selects one of the trending risk factors in Operation 1220 and determines the opportunity cost for any instances of behaviors found in the behavioral pattern prediction model 320 that contribute to the risk factor in Operation 1225. As previously discussed, the module may perform this operation in particular embodiments by dividing the average OOP cost for the risk factor by the threshold for the behavior contributing to the risk factor as defined in a corresponding clinical risk rule data object to determine a cost per unit for the behavior. The module may then multiply the cost per unit by the number of units involved in the instance of the behavior to arrive at an opportunity cost for the particular instance of the behavior.

For example, the risk model 340 may indicate the end user is trending towards obesity. In addition, the behavioral pattern prediction model 320 may identify an occurrence of the end user consuming a sugary food item (e.g., a donut). A clinical risk rule data object may be defined for obesity that consuming 2,700 grams of sugar over a three-month period leads to obesity and the average OOP cost for becoming obese is $435. Accordingly, the risk evaluation module may determine a per unit cost of consuming a gram of sugar with respect to becoming obese is $0.16 ($435/2, 700 grams). The amount of sugar in the sugary food item consumed during the occurrence may be determined to be 11 grams. Therefore, the risk evaluation module may determine the opportunity cost for consuming the sugary food item is $1.76.

At this point, the risk evaluation module determines whether the end user is trending towards another risk factor in Operation 1230. If so, then the risk evaluation module returns to Operation 1220, selects the next trending risk factor, and determines the opportunity cost for any behaviors found in the behavioral pattern prediction model 320 contributing to the trending risk factor. Once the risk evaluation module has determined the opportunity costs for each of the trending risks, the risk evaluation module has a message sent to the end user informing the user of the opportunity cost of his or her instance(s) of behavior(s) in Operation 1235. For example, in particular embodiments, the risk evaluation module may have a message display through a software application residing on a device of the user. The message may inform the user that "Consuming this sugary food item may increase your future contributions by $1.76." Therefore, the message may communicate to the end user the consequences of his or her behavior(s) and may lead the user to making better choices with respect to the behavior(s).

Contribution Module

Figure 13:
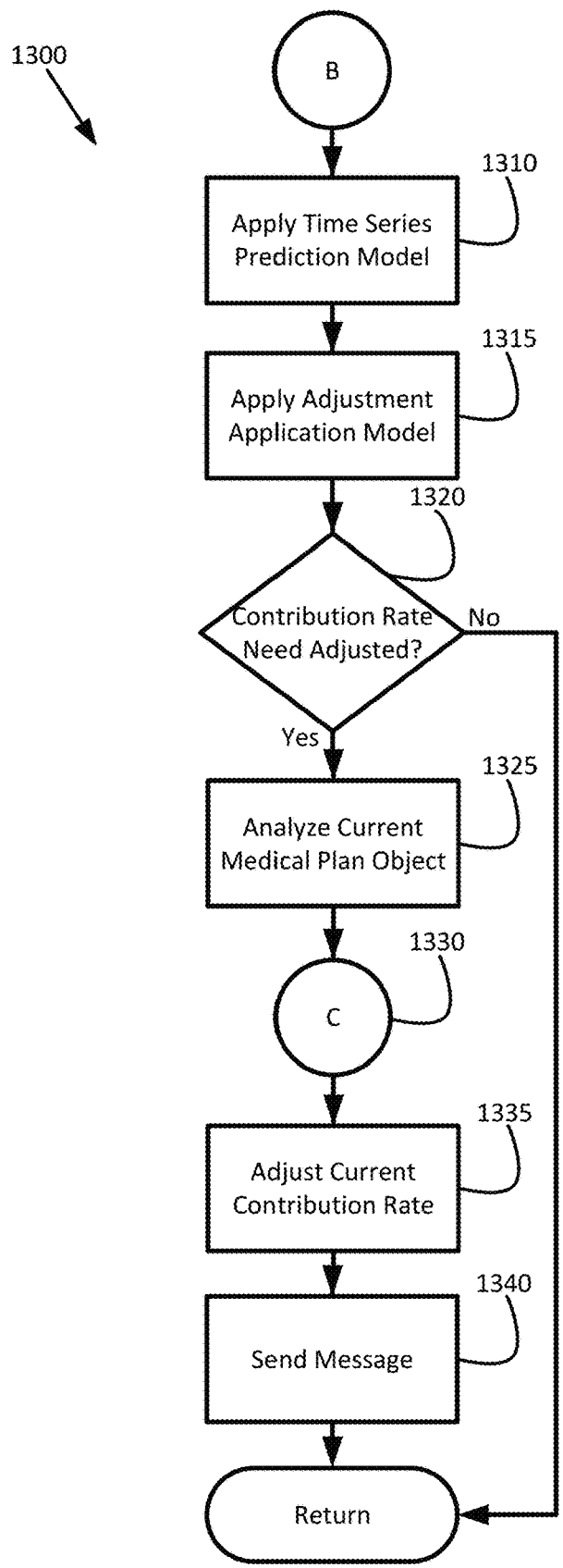
FIG. 13 is a process flow for evaluating a current contribution rate used for a financial instrument in accordance with various embodiments of the present disclosure.

Turning now to FIG. 13, additional details are provided for assessing an end user's current contribution rate to a financial instrument in light of one or more trending risk factor(s) according to various embodiments. FIG. 13 is a flow diagram showing a contribution module for performing such functionality according to various embodiments of the disclosure. As previously mentioned, the contribution module may be invoked by another module in particular embodiments to assess the end user's current contribution rate such as, for example, the remote monitoring module previously described. However, with that said, the contribution module may not necessarily be invoked by another module and may execute as a stand-alone module in other embodiments.

As previously discussed, various embodiments involve evaluating an end user's current contribution rate to a financial instrument in which the funds found in the instrument are used to pay for OOP expenses for medical conditions. For example, such an instrument may be an HSA. In particular, such an evaluation is carried out in response to finding the end user is trending towards one or more risk factors that may contribute to him or her developing one or more medical conditions. Therefore, the user's current contribution rate and current balance found in the instrument are evaluated to determine whether the current contribution rate should be modified to cover additional medical expenses that may arise due to any medical conditions the user may develop as a result of the trending risk factors.

The process flow 1300 begins with the contribution module determining whether a change in the end user's current contribution rate should be instituted in light of the potential medical condition(s) that may result from the trending risk factor(s). As previously discussed, an adjustment generating machine learning model 355 is used in various embodiments to generate an adjustment model 360 for the end user based on the generated risk model 340 and the adjustment model 360 indicates whether the contribution to the financial instrument needs to be increased based on the per-risk factor scores described by the risk model 340.

As previously noted, the adjustment generation machine learning model 355 in some embodiments may comprise a time series prediction model and an adjustment application model. The time series prediction model is configured to determine a projected balance of the end user's financial instrument over a prospective period of time, and the adjustment application model is configured to generate the adjustment model 360 based on the projected balance and the risk model 340. Therefore, in these embodiments, the contribution module applies the time series prediction model in Operation 1310 to determine a projected balance of the end user's financial instrument over a prospective period of time and then processes the projected balance and risk model 340 using the adjustment application model to generate the adjustment model 360 for the end user in Operation 1315. In turn, the adjustment model 360 indicates whether the contribution to the financial instrument needs to be adjusted (e.g., increased).

Therefore, the contribution module determines whether the current contribution rate needs to be adjusted based on the adjustment model 360 in Operation 1320. If so, then the contribution module analyzes a current medical plan object detailing the end user's current medical insurance in Operation 1325. Such analysis is performed in particular embodiments to determine what OOP expenses the end user is obligated to pay based on the end user's medical insurance benefits. For example, the end user's OOP expenses are typically higher if the user is enrolled in a HDHP than if the user were enrolled in a low-deductible health plan. In addition, OOP expenses can be different depending on whether the end user is enrolled in a health maintenance organization (HMO) plan versus a preferred provider organization (PPO) plan. Typically, a HMO plan results in lower cost than a PPO plan. Further, some individuals may not have any medical insurance. In addition, many medical insurance plans will cap an individual's OOP expenses for a year.

Next, the contribution module determines the required contribution amount needed to pay the OOP medical expenses that the end user could incur due to the medical condition(s) that may develop based on the trending risk factor(s) in Operation 1330. Here, in particular embodiments, the contribution module performs this operation by invoking a contribution calculator module (FIG. 14) and in turn, the contribution calculator module determines the required contribution amount needed to cover the expected OOP expenses. The contribution module then adjusts the current contribution rate based on the required contribution amount in Operation 1335.

In adjusting the current contribution rate, the contribution module may be configured in some embodiments to take into consideration any legal and/or policy restrictions placed on making contributions to the financial instruments. For example, a policy may be in place on the instrument restricting frequent changes to the current contribution rate. Therefore, the contribution module may be configured to use some mechanism such as an internal ledger to facilitate adjusting the current contribution rate to the appropriate rate. In addition, depending on the circumstances, the contribution module may be configured to make the adjustment automatically or only after approval of the end user. For instance, during the setup for monitoring, the end user may indicate whether or not he or she would like adjustments made to his or her current contribution rate to be made automatically or only once he or she has approved the adjustments.

The contribution module concludes the adjustment of the current contribution rate by sending a message to the user informing him or her of the adjustment in Operation 1340. In some instances, the message may also request the user's consent to making the adjustment.

Contribution Calculator Module

Figure 14:
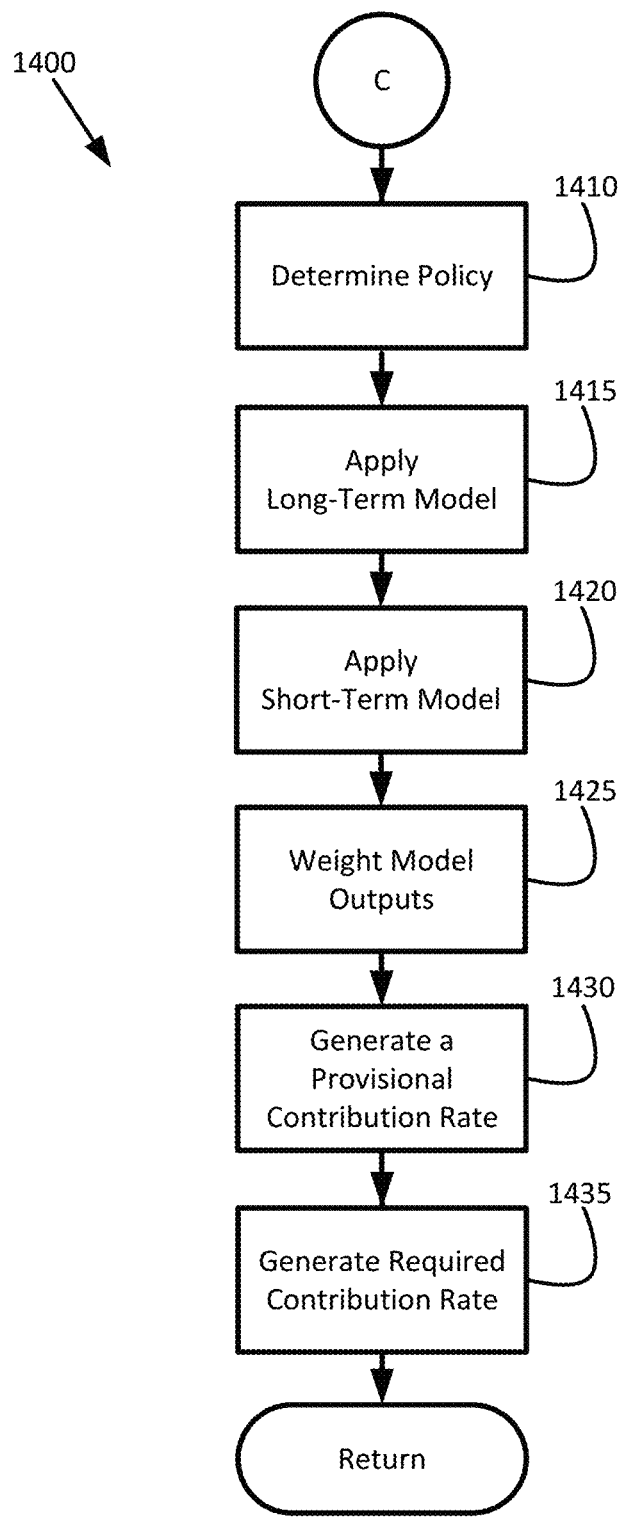
FIG. 14 is a process flow for determining a required contribution amount for one or more potential medical conditions in accordance with various embodiments of the present disclosure.

Turning now to FIG. 14, additional details are provided for determining the required contribution amount needed to cover OOP expenses expected to be incurred by an end user for one or more potential medical condition(s) that may develop due to the user's trending risk factor(s) according to various embodiments. FIG. 14 is a flow diagram showing a contribution calculator module for performing such functionality according to various embodiments of the disclosure. As previously mentioned, the contribution calculator module may be invoked by another module in particular embodiments to determine a required contribution amount for the end user such as, for example, the contribution module previously described. However, with that said, the contribution calculator module may not necessarily be invoked by another module and may execute as a standalone module in other embodiments.

As previously discussed, one or more contribution models may be employed in various embodiments to determine the required contribution amount to properly fund the end user's financial instrument to adequately cover OOP expenses that he or she may incur as a result of the medical condition(s) that may develop due to the trending risk factor(s). Accordingly, a long-term model may be developed to account for potential medical conditions that are considered as long-term conditions. For instance, type 2 diabetes is normally considered a long-term health condition. As previously noted, the long-term model is configured to optimize contributions over a long time horizon. Therefore, this particular model is generally configured to better account for (fund expenses for) medical conditions may be deemed long-term conditions.

In addition, a short-term model may be developed to account for potential medical conditions that are considered be short-term conditions such as, for example, a cavity. As previously noted, the short-term model is configured to cover the OOP maximum expense in each year, subject to any policies associated with the financial instrument (e.g., subject to an annual contribution limit). Therefore, this particular model is generally configured to better account for (fund expenses for) medical conditions that occur in/over a short time period.

Therefore, the process flow 1400 begins with the contribution calculator module determining the policy associated with the end user's financial instrument in Operation 1410. For example, the policy may indicate a maximum annual contribution is set for the instrument such as those set on HSAs. Accordingly, any such policy may be used as input to one or more of the models. The contribution calculator module then applies the long-term and short-term models in Operations 1415 and 1420 to produce a first output and a second output, where each of the two outputs provide a needed contribution amount based on their respective models and the medical condition(s) that may develop due to the trending risk factor(s).

The contribution calculator module then weights the two outputs in Operation 1425 in accordance with the potential medical condition(s) based on their long-term and short-term effects on OOP expenses that may be incurred by the end user. For example, if the two medical conditions that may develop due to the end user's trending risk factor(s) are type 2 diabetes and a cavity, then the contribution calculator module may weight the output from the long-term model more heavily since a user who has developed type 2 diabetes may incur OPP expenses for a number of years due to this condition. On the other hand, if the only potential medical condition due to the end user's trending risk factor(s) is a cavity, then the contribution calculator may weight the output from the short-term model more heavily since the end user is expected to only incur a onetime expense for this condition. The contribution calculator module then generates a provisional contribution amount by combining the two weighted outputs in Operation 1430.

At this point, the contribution calculator module uses the provisional contribution amount to modify a base contribution amount that is based on the potential medical condition(s) to determine a required contribution amount to cover the end user's expected OOP expenses due to the condition(s) in Operation 1435. Here, in particular embodiments, the contribution calculator module may determine the base contribution amount from contribution amounts acquired from a mechanism such as, for example, a lookup table and/or the like. Accordingly, the contribution amounts found in the lookup table for each of the potential medical conditions may be established based on historical data on expenses associated with treating each of the conditions.

Examples of Messages

Figure 15:
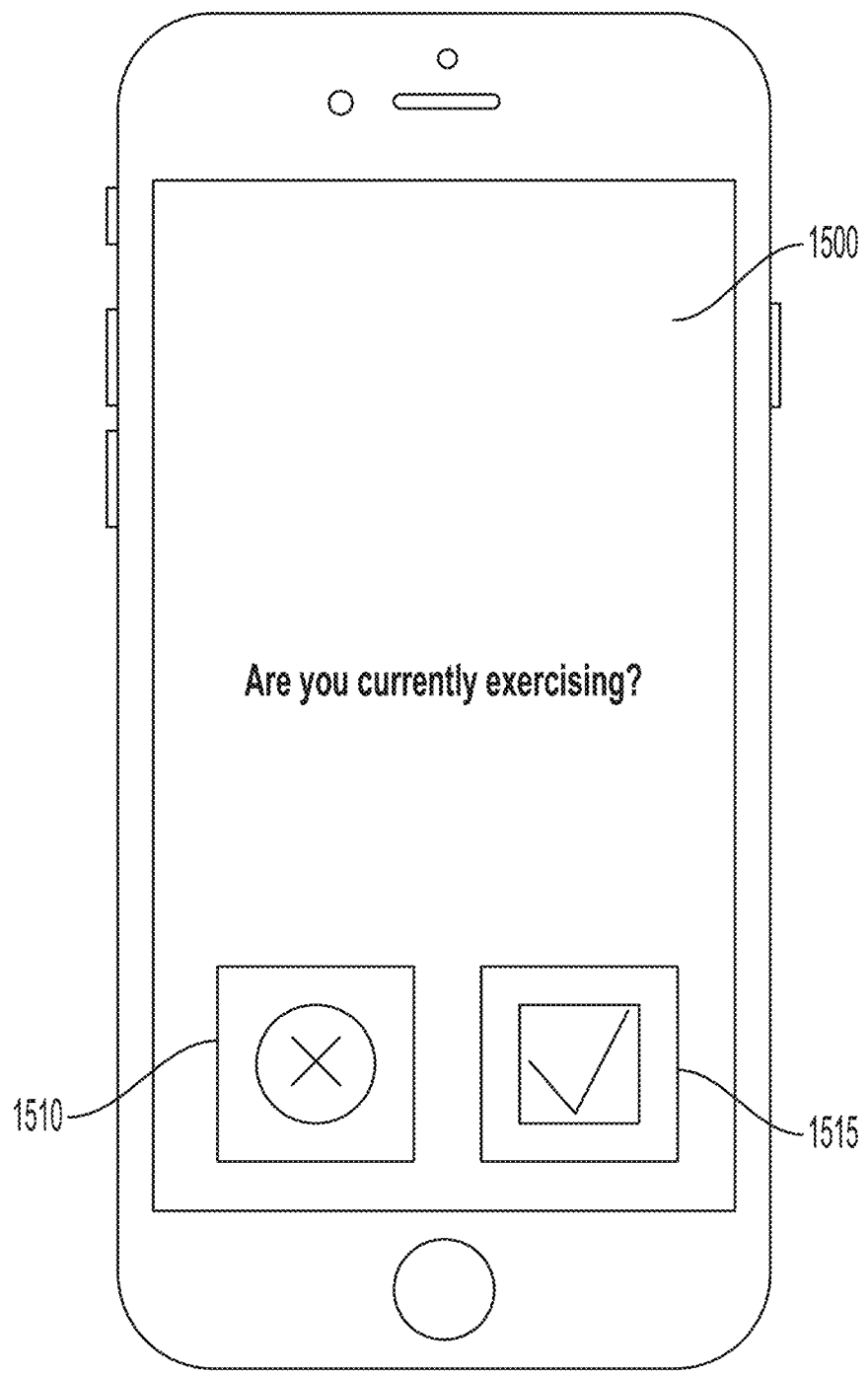
FIG. 15 is an example of displaying a message on a mobile device in accordance with various embodiments of the present disclosure.
Figure 16:
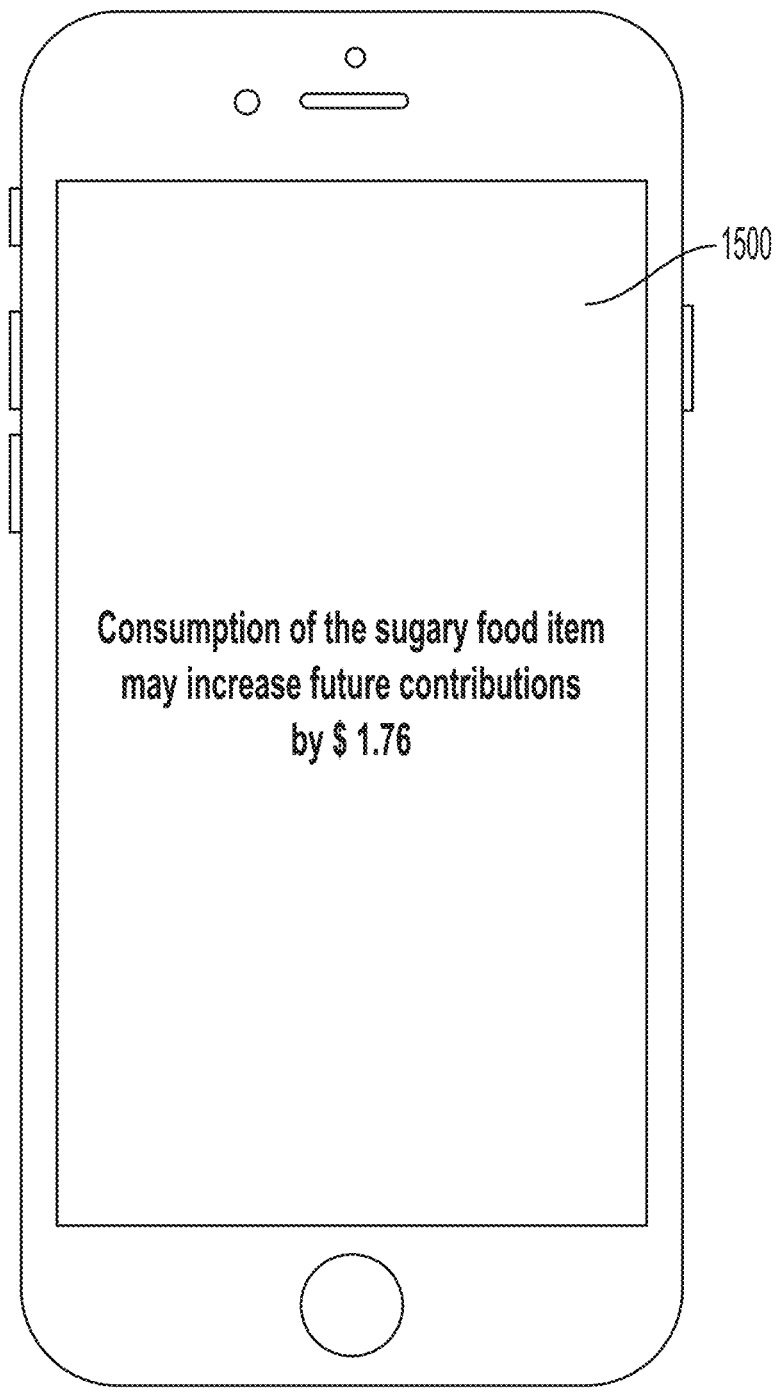
FIG. 16 is another example of displaying a message on a mobile device in accordance with various embodiments of the present disclosure.

FIGS. 15 and 16 provide two examples of messages that may be displayed on an end user's mobile device 505 in accordance with various embodiments. Specifically, FIG. 15 provides an example of a message that may be displayed on an end user's mobile device 505 asking the end user whether he or she is participating in a particular behavior. In this instance, the end user is participating in a behavior that is generally viewed as a positive contributor to the user's current health state. Accordingly, the screen 1500 of the device is displaying a message asking the end user if he or she is currently exercising. Such a message may be displayed to confirm the end user's behavior after detecting one or more behavioral monitoring data objects indicating the behavior. For example, the end user's mobile device 505 may be communicating with a fitness tracker 507 being worn by the end user that tracks physical activity. The message is asking the end user to confirm whether he or she is participating in exercising by selecting the appropriate button 1510, 1515 on the screen.

FIG. 16 provides an example of a message displayed on the screen 1500 of the mobile device 505 informing the end user that by consuming a sugary food item, the end user could increase his or her future contributions to a financial instrument by $1.76. Here, FIG. 16 is an example of providing the end user with an opportunity cost associated with participating in an instance of a particular behavior. Accordingly, such messages can serve as a deterrence with respect to the end user taking part in behaviors that may lead to developing risk factors that may contribute to various medical conditions.

Conclusion

Many modifications and other embodiments of the disclosure set forth herein will come to mind to one skilled in the art to which these modifications and other embodiments pertain having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
   receiving, by one or more processors, one or more behavioral monitoring data objects generated by one or more distributed behavioral monitoring devices;
   generating, by the one or more processors and using a behavioral pattern prediction model, one or more behavior data objects, wherein: (i) the one or more behavior data objects identify occurrences of an end user participating in one or more behaviors based at least in part on inferencing occurrences of the end user participating in the one or more behaviors, (ii) the behavioral pattern prediction model is generated by a behavioral pattern prediction machine learning model based at least in part on the one or more behavioral monitoring data objects, and (iii) the one or more behavior data objects are associated with one or more risk factors;
   determining, by the one or more processors and using one or more risk models, one or more per-risk factor scores associated with progression towards respective ones of the one or more risk factors based at least in part on the one or more behavior data objects, wherein: (i) the one or more risk models are generated by a risk generation machine learning model based at least in part on an effect of the one or more behavior data objects on the one or more risk factors and (ii) the effect of the one or more behavior data objects on the one or more risk factors is based at least in part on one or more thresholds for respective ones of the one or more behavior data objects to affect the one or more risk factors;
   determining, by the one or more processors and using an adjustment model, an adjustment to a contribution rate, wherein: (i) the adjustment model is generated by an adjustment generation machine learning model based at least in part on the one or more risk models and (ii) the adjustment is based at least in part on (a) a compensation associated with the progression towards the one or more risk factors, (b) one or more adjustment values associated with respective ones of the one or more per-risk factor scores, and (c) one or more weights associated with respective ones of the one or more per-risk factor scores, wherein the one or more weights are generated based at least in part on (1) a long-term effect and a short-term effect on the contribution rate associated with a respective one of the one or more risk factors, (2) a long-term model configured to optimize contributions over a first time period, and (3) a short-term model configured to optimize contributions over a second time period that is shorter than the first time period; and
   initiating, by the one or more processors, the performance of one or more prediction-based actions based at least in part on the adjustment.

2. The computer-implemented method of claim 1, wherein the risk generation machine learning model is configured to generate the one or more risk models by:
   generating a general risk model based at least in part on the one or more behavior data objects;
   generating an individual risk model based at least in part on the one or more behavior data objects in relation to the end user; and
   combining the general risk model and the individual risk model.

3. The computer-implemented method of claim 1, wherein the adjustment generation machine learning model comprises a time series prediction model and an adjustment application model.

4. The computer-implemented method of claim 3, wherein the adjustment generation machine learning model generates the adjustment model by:
   determining a projected contribution for a prospective period of time by using the time series prediction model; and
   generating the adjustment model based at least in part on the projected contribution, the one or more risk models, and the adjustment application model.

5. The computer-implemented method of claim 1, wherein the one or more prediction-based actions comprise automatically adjusting a current contribution rate to a financial instrument based at least in part on the adjustment model.

6. The computer-implemented method of claim 1, wherein the one or more risk factors are determined based at least in part on one or more medical conditions applicable to the end user and the computer-implemented method further comprises:
identifying the one or more medical conditions based at least in part on a health profile data object for the end user and a medical conditions prediction machine learning model, wherein the medical conditions prediction machine learning model is configured to identify a probability for each medical condition of a plurality of medical conditions representative of a likelihood of the end user developing the medical condition.

7. The computer-implemented method of claim 5, wherein the financial instrument is at least one of a health savings account (HSA) or a flexible spending account (FSA).

8. A system comprising memory and one or more processors configured to:
receive one or more behavioral monitoring data objects generated by one or more distributed behavioral monitoring devices;
generate, using a behavioral pattern prediction model, one or more behavior data objects, wherein: (i) the one or more behavior data objects identify occurrences of an end user participating in one or more behaviors based at least in part on inferencing occurrences of the end user participating in the one or more behaviors, (ii) the behavioral pattern prediction model is generated by a behavioral pattern prediction machine learning model based at least in part on the one or more behavioral monitoring data objects, and (iii) the one or more behavior data objects are associated with one or more risk factors;
determine, using one or more risk models, one or more per-risk factor scores associated with progression towards respective ones of the one or more risk factors based at least in part on the one or more behavior data objects, wherein: (i) the one or more risk models are generated by a risk generation machine learning model based at least in part on an effect of the one or more behavior data objects on the one or more risk factors and (ii) the effect of the one or more behavior data objects on the one or more risk factors is based at least in part on one or more thresholds for respective ones of the one or more behavior data objects to affect the one or more risk factors;
determine, using an adjustment model, an adjustment to a contribution rate, wherein: (i) the adjustment model is generated by an adjustment generation machine learning model based at least in part on the one or more risk models and (ii) the adjustment is based at least in part on (a) a compensation associated with the progression towards the one or more risk factors, (b) one or more adjustment values associated with respective ones of the one or more per-risk factor scores, and (c) one or more weights associated with respective ones of the one or more per-risk factor scores, wherein the one or more weights are generated based at least in part on (1) a long-term effect and a short-term effect on the contribution rate associated with a respective one of the one or more risk factors, (2) a long-term model configured to optimize contributions over a first time period, and (3) a short-term model configured to optimize contributions over a second time period that is shorter than the first time period; and
initiate the performance of one or more prediction-based actions based at least in part on the adjustment.

9. The system of claim 8, wherein the risk generation machine learning model is configured to generate the one or more risk models by:
generating a general risk model based at least in part on the one or more behavior data objects;
generating an individual risk model based at least in part on the one or more behavior data objects in relation to the end user; and
combining the general risk model and the individual risk model.

10. The system of claim 8, wherein the adjustment generation machine learning model comprises a time series prediction model and an adjustment application model.

11. The system of claim 10, wherein the adjustment generation machine learning model generates the adjustment model by:
determining a projected contribution for a prospective period of time by using the time series prediction model; and
generating the adjustment model based at least in part on the projected contribution and the one or more risk models.

12. The system of claim 8, wherein the one or more prediction-based actions comprise automatically adjusting a current contribution rate to a financial instrument based at least in part on the adjustment model.

13. The system of claim 8, wherein the one or more risk factors are determined based at least in part on one or more medical conditions applicable to the end user and the one or more processors are further configured to:
identify the one or more medical conditions based at least in part on a health profile data object for the end user and a medical conditions prediction machine learning model, wherein the medical conditions prediction machine learning model is configured to identify a probability for each medical condition of a plurality of medical conditions representative of a likelihood of the end user developing the medical condition.

14. The system of claim 12, wherein the financial instrument is at least one of a health savings account (HSA) or a flexible spending account (FSA).

15. One or more non-transitory computer-readable storage media including instructions that cause one or more processors to:
receive one or more behavioral monitoring data objects generated by one or more distributed behavioral monitoring devices;
generate, using a behavioral pattern prediction model, one or more behavior data objects, wherein: (i) the one or more behavior data objects identify occurrences of an end user participating in one or more behaviors based at least in part on inferencing occurrences of the end user participating in the one or more behaviors, (ii) the behavioral pattern prediction model is generated by a behavioral pattern prediction machine learning model based at least in part on the one or more behavioral monitoring data objects, and (iii) the one or more behavior data objects are associated with one or more risk factors;

determine, using one or more risk models, one or more per-risk factor scores associated with progression towards respective ones of the one or more risk factors based at least in part on the one or more behavior data objects, wherein: (i) the one or more risk models are generated by a risk generation machine learning model based at least in part on an effect of the one or more behavior data objects on the one or more risk factors and (ii) the effect of the one or more behavior data objects on the one or more risk factors is based at least in part on one or more thresholds for respective ones of the one or more behavior data objects to affect the one or more risk factors;

determine, using an adjustment model, an adjustment to a contribution rate, wherein: (i) the adjustment model is generated by an adjustment generation machine learning model based at least in part on the one or more risk models and (ii) the adjustment is based at least in part on (a) a compensation associated with the progression towards the one or more risk factors, (b) one or more adjustment values associated with respective ones of the one or more per-risk factor scores, and (c) one or more weights associated with respective ones of the one or more per-risk factor scores, wherein the one or more weights are generated based at least in part on (1) a long-term effect and a short-term effect on the contribution rate associated with a respective one of the one or more risk factors, (2) a long-term model configured to optimize contributions over a first time period, and (3) a short-term model configured to optimize contributions over a second time period that is shorter than the first time period; and initiate the performance of one or more prediction-based actions based at least in part on the adjustment.

16. The one or more non-transitory computer-readable storage media of claim 15, wherein the risk generation machine learning model is configured to generate the one or more risk models by:

generating a general risk model based at least in part on the one or more behavior data objects;

generating an individual risk model based at least in part on the one or more behavior data objects in relation to the end user; and combining the general risk model and the individual risk model.

17. The one or more non-transitory computer-readable storage media of claim 15, wherein the adjustment generation machine learning model comprises a time series prediction model and an adjustment application model.

18. The one or more non-transitory computer-readable storage media of claim 17, wherein the adjustment generation machine learning model generates the adjustment model by:

determining a projected contribution for a prospective period of time by using the time series prediction model; and generating the adjustment model based at least in part on the projected contribution and the one or more risk models.

19. The one or more non-transitory computer-readable storage media of claim 17, wherein the one or more prediction-based actions comprise automatically adjusting a current contribution rate to a financial instrument based at least in part on the adjustment model.

20. The one or more non-transitory computer-readable storage media of claim 15, wherein the one or more risk factors are determined based at least in part on one or more medical conditions applicable to the end user and the one or more processors are further caused to:

identify the one or more medical conditions based at least in part on a health profile data object for the end user and a medical conditions prediction machine learning model, wherein the medical conditions prediction machine learning model is configured to identify a probability for each medical condition of a plurality of medical conditions representative of a likelihood of the end user developing the medical condition.

* * * * *